United States Patent [19]
Toda

[11] Patent Number: 5,754,498
[45] Date of Patent: May 19, 1998

[54] SYSTEM FOR MEASURING ULTRASOUND TRANSMISSION IN MATERIALS

[76] Inventor: Kohji Toda, 1-49-18 Futaba, Yokosuka 239, Japan

[21] Appl. No.: 757,345

[22] Filed: Nov. 27, 1996

[51] Int. Cl.$^6$ .................................................. G01N 29/04
[52] U.S. Cl. .............................. 367/137; 73/589; 73/597; 73/599; 73/602; 73/624
[58] Field of Search ........................... 73/571, 574, 589, 73/597, 599, 602, 624; 367/137

[56] References Cited

U.S. PATENT DOCUMENTS

| | | | |
|---|---|---|---|
| 4,481,820 | 11/1984 | Thomann | 73/597 |
| 4,581,935 | 4/1986 | Breazeale | 73/599 |
| 5,348,009 | 9/1994 | Ohtomo et al. | 128/653.1 |
| 5,665,907 | 9/1997 | Sheen et al. | 73/159 |

*Primary Examiner*—J. Woodrow Eldred

[57] ABSTRACT

A system for ultrasound transmission in materials comprising a reference unit, an examination unit, at least a case equipped in at least the examination unit, and a signal processing unit. The reference unit consists of at least an input ultrasonic transducer $T_o$ and at least an output ultrasonic transducer $R_o$. The examination unit consists of at least an input ultrasonic transducer $T_s$ and at least an output ultrasonic transducer $R_s$. The case is placed between the ultrasonic transducers $T_s$ and $R_s$. The signal processing unit is connected with output terminals of the ultrasonic transducers $R_o$ and $R_s$. When electric signals are applied to the ultrasonic transducers $T_o$ and $T_s$, ultrasounds are emitted in air from the ultrasonic transducers $T_o$ and $T_s$, respectively, and then received by the ultrasonic transducers $R_o$ and $R_s$, respectively. If a group of fibers or leaf fragments wrapped in paper or others is placed in case 1, the ultrasound emitted from the ultrasonic transducer $T_s$ goes through the group of fibers or leaf fragments. Therefore, an output electric signal delivered from the ultrasonic transducer $R_s$ is decreased, causing a difference between the output electric signal delivered from the ultrasonic transducer $R_s$ and that delivered from the ultrasonic transducer $R_o$. The difference is detected by the signal processing unit 3 and compared with that corresponding to a standard group of fibers or leaf fragments. Thus, a filling-density of the group of fibers or leaf fragments examined is evaluated.

12 Claims, 17 Drawing Sheets

5,754,498

SYSTEM FOR MEASURING ULTRASOUND TRANSMISSION IN MATERIALS

BACKGROUND OF THE INVENTION

1. Field of the Invention.

The present invention relates to an ultrasonic system for measuring a filling-density of a group of fibers, leaf fragments and so on.

2. Description of the Prior Art.

A conventional method for measuring a filling-density of a group of leaf fragments is based on a radiant-ray examination requiring technical skill and having some problems on security, management and maintenance.

Attempts to measure a filling-density of a group of fibers or leaf fragments by making use of an ultrasound emitted in air are regarded to be very difficult. Ultrasounds emitted in air by conventional ultrasonic transducers require essential means for overcoming the influence of surroundings such as temperature change. If measuring a filling-density of a group of fibers or leaf fragments, at least an input ultrasonic transducer emitting an ultrasound in air and at least an output ultrasonic transducer receiving the ultrasound are necessary, the group of fibers or leaf fragments being placed between the input and output ultrasonic transducers. However, it was very difficult to measure precisely the filling-density by using the conventional ultrasonic transducers because of the weak intensity of the ultrasound under the influence of temperature change, moisture change and so on. Accordingly, a reference unit with input and output ultrasonic transducers, an examination unit with input and output ultrasonic transducers, and a signal processing unit are provided in the application, a group of fibers or leaf fragments being located between the input and output ultrasonic transducers of the examination unit, the signal processing unit detecting a difference between the output electric signals of reference and examination units and comparing the difference with a standard group of fibers or leaf fragments and evaluating a filling-density of an examination group of fibers or leaf fragments.

SUMMARY OF THE INVENTION

An object of the present invention is to provide a system for measuring ultrasound transmission in materials capable of measuring a filling-density of a group of fibers, leaf fragments and so on under low power consumption and low voltage.

Another object of the present invention is to provide a system for measuring ultrasound transmission in materials capable of measuring a filling-density of a group of fibers, leaf fragments and so on securely, precisely and quickly.

Another object of the present invention is to provide a system for measuring ultrasound transmission in materials being easy to operate and maintain.

A still other object of the present invention is to provide a system for ultrasound transmission in materials excellent in durability.

A still further object of the present invention is to provide a system for ultrasound transmission in materials with a small size which is very light in weight and has a simple structure.

According to one aspect of the present invention there is provided a system for ultrasound transmission in materials comprising a reference unit, an examination unit, at least a case equipped in at least the examination unit, and a signal processing unit. The reference unit consists of at least an input ultrasonic transducer $T_o$ and at least an output ultrasonic transducer $R_o$ opposed to the ultrasonic transducer $T_o$. The examination unit consists of at least an input ultrasonic transducer $T_s$ and at least an output ultrasonic transducer $R_s$ opposed to the ultrasonic transducer $T_s$. The case is placed between the ultrasonic transducers $T_s$ and $R_s$, and has an examination group of fibers or leaf fragments therein. The signal processing unit is connected with output terminals of the ultrasonic transducers $R_o$ and $R_s$.

When electric signals are applied to the ultrasonic transducers $T_o$ and $T_s$, respectively, ultrasounds are emitted in air from the ultrasonic transducer $T_o$ and $T_s$, respectively. The ultrasound emitted from the ultrasonic transducer $T_o$ is received by the ultrasonic transducer $R_o$, and delivered as an output electric signal from the ultrasonic transducer $R_o$. The ultrasound emitted from the ultrasonic transducer $T_s$ goes through the examination group of fibers or leaf fragments, and then, the ultrasound is received by the ultrasonic transducer $R_s$, and delivered as an output electric signal from the ultrasonic transducer $R_s$. Therefore, the output electric signal delivered from the ultrasonic transducer $R_s$ is decreased, causing a difference between the output electric signals delivered from the ultrasonic transducer $R_s$ and $R_o$. The difference is detected by the signal processing unit and compared with that corresponding to a standard group of fibers or leaf fragments. Thus, a filling-density of the examination group of fibers or leaf fragments is evaluated.

According to another aspect of the present invention there is provided an amplifier. An output terminal of the ultrasonic transducer $R_o$ is connected with input terminals of the ultrasonic transducers $T_o$ and $T_s$ via the amplifier. The ultrasonic transducers $T_o$, $R_o$ and the amplifier form an oscillator with an ultrasonic propagation lane, as a delay element, between the ultrasonic transducers $T_o$ and $R_o$.

According to other aspect of the present invention there is provided a signal processing unit comprising a phase comparator. The phase comparator detects a phase difference between the output electric signals delivered from the ultrasonic transducers $R_o$ and $R_s$, compares the phase difference with that corresponding to the standard group of fibers or leaf fragments, and evaluates a filling-density of the examination group of fibers or leaf fragments.

According to further aspect of the present invention there is provided a system for ultrasound transmission in materials comprising a reference unit, an examination unit, and a signal processing unit. The reference unit consists of at least an input ultrasonic transducer $T_o$, at least an output ultrasonic transducer $R_o$ corresponding with the ultrasonic transducer $T_o$, and a reference case having a concavity therein. The examination unit consists of at least an input ultrasonic transducer $T_s$, at least an output ultrasonic transducer $R_s$ corresponding with the ultrasonic transducer $T_s$, and an examination case with a concavity therein and having an examination group of fibers or leaf fragments on the concavity. The signal processing unit is connected with output terminals of the ultrasonic transducers $R_o$ and $R_s$.

When electric signals are applied to the ultrasonic transducers $T_o$ and $T_s$, respectively, ultrasounds are emitted in air from the ultrasonic transducer $T_o$ and $T_s$, respectively. The ultrasound emitted from the ultrasonic transducer $T_o$ is reflected by the concavity of the reference case, received by the ultrasonic transducer $R_o$, and delivered as an output electric signal from the ultrasonic transducer Ro. The ultrasound emitted from the ultrasonic transducer $T_s$ is reflected by the concavity of the examination case, received by the ultrasonic transducer $R_s$, and delivered as an output electric signal from the ultrasonic transducer $R_s$. In this time, the ultrasound emitted from the ultrasonic transducer $T_s$ goes through the examination group of fibers or leaf fragments twice. Therefore, the output electric signal delivered from the ultrasonic transducer $R_s$ is decreased, causing a difference between the output electric signals delivered from the ultrasonic transducer $R_s$ and $R_o$. The difference is detected by the signal processing unit and compared with that corresponding to a standard group of fibers or leaf fragments. Thus, a filling-density of the examination group of fibers or leaf fragments is evaluated.

BRIEF DESCRIPTION OF THE DRAWINGS

Other features and advantages of the invention will be clarified from the following description with reference to the attached drawings.

DETAILED DESCRIPTION OF THE PRESENTLY PREFERRED EXEMPLARY EMBODIMENTS

Figure 1:
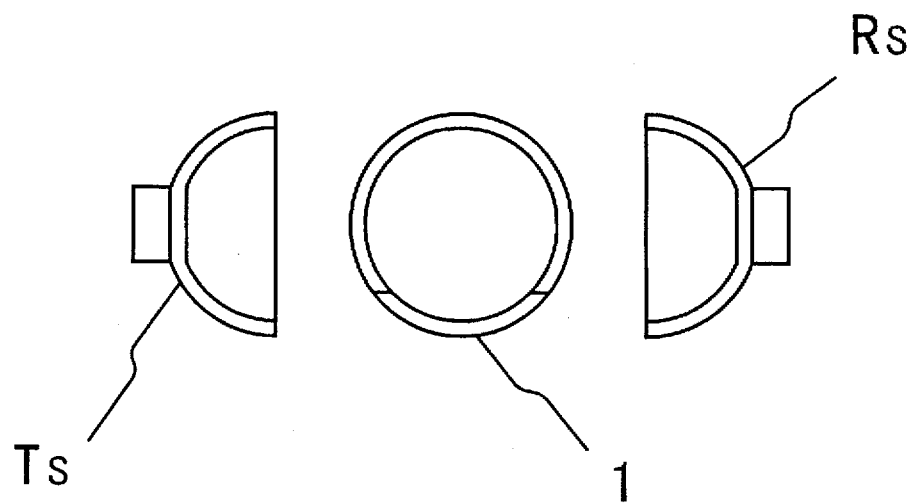
FIG. 1 shows a sectional view of the system for ultrasound transmission in materials according to a first embodiment of the present invention.

FIG. 1 shows a sectional view of a system for ultrasound transmission in materials according to a first embodiment of the present invention. The system for ultrasound transmission in materials comprises ultrasonic transducers $T_o$, $R_o$, $T_s$, $R_s$, case 1 placed between ultrasonic transducers $T_s$ and $R_s$, amplifier 2 and signal processing unit 3 comprising a differential amplifier. FIG. 1 shows only ultrasonic transducers $T_s$, $R_s$ and case 1. Ultrasonic transducers $T_o$, $R_o$, $T_s$ and $R_s$ are made from the same material each other, and have the same cone construction having the center frequency of 39.2 kHz and the cone diameter of 1 cm. Both the distance between ultrasonic transducers $T_o$ and $R_o$, and the distance between ultrasonic transducers $T_s$ and $R_s$ are 4.95 cm. When operating, a group of fibers or leaf fragments is placed in case 1. The relative position of ultrasonic transducer $T_o$ to ultrasonic transducer $R_o$ is equal to that of ultrasonic transducer $T_s$ to ultrasonic transducer $R_s$. Case 1 is not always placed between ultrasonic transducers $T_o$ and $R_o$.

Figure 2:
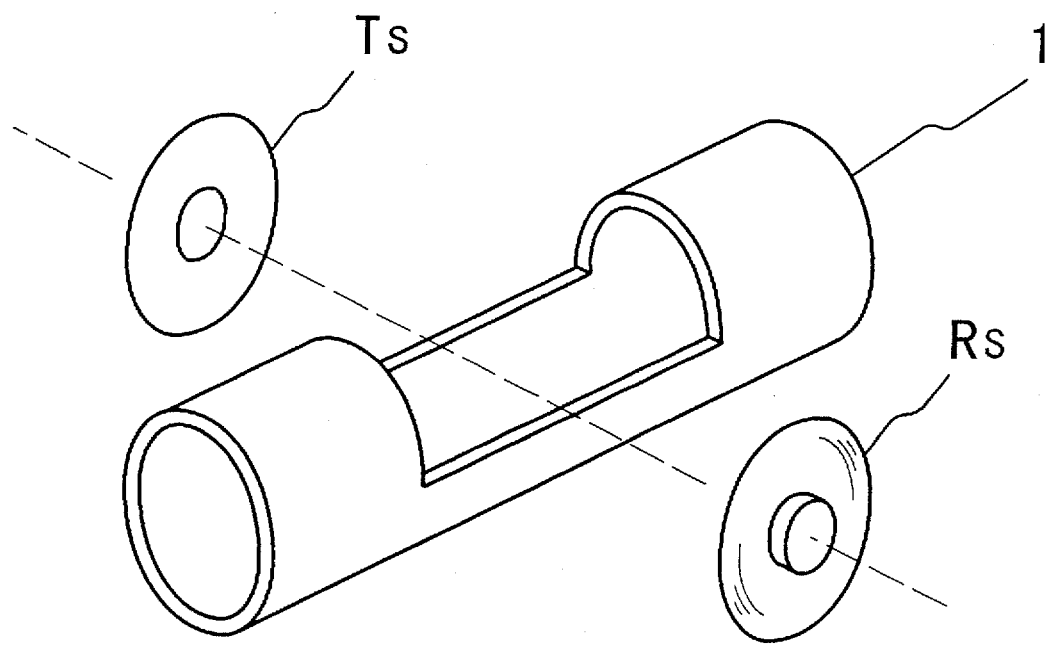
FIG. 2 shows a perspective view of ultrasonic transducers $T_s$, $R_s$ and case 1.

FIG. 2 shows a perspective view of ultrasonic transducers $T_s$, $R_s$ and case 1. Case 1 has a cylindrical structure with the cylindrical diameter of 1 cm and having an opening at the top thereof for the purpose of ultrasound transmission. If case 1 has no opening, it is necessary for case 1 to be made from a material such that an ultrasound is easy to go through the material.

Figure 3:
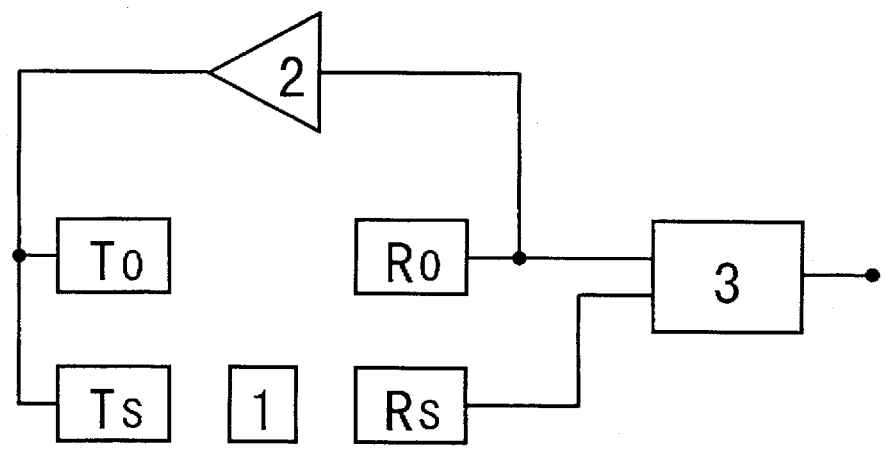
FIG. 3 shows a diagram of a driving circuit of the system for ultrasound transmission in materials in FIG. 1.

FIG. 3 shows a diagram of a driving circuit of the system for ultrasound transmission in materials in FIG. 1. Signal processing unit 3 to obtain an output electric signal is connected with output terminals of ultrasonic transducers $R_o$ and $R_s$. When operating the system for ultrasound transmission in materials in FIG. 1, an electric signal is applied to ultrasonic transducer $T_o$. In this time, an ultrasound is emitted in air from the cone center of ultrasonic transducer $T_o$. The ultrasound is received by ultrasonic transducer $R_o$, and is delivered as an output electric signal from ultrasonic transducer $R_o$. In the same way, when an electric signal is applied to ultrasonic transducer $T_s$, an ultrasound is emitted in air from the cone center of ultrasonic transducer $T_s$, and is received by ultrasonic transducer $R_s$ and delivered as an output electric signal from ultrasonic transducer $R_s$. If a group of fibers or leaf fragments wrapped in paper or others is placed in case 1, the ultrasound emitted from ultrasonic transducer $T_s$ goes through the group of fibers or leaf fragments. Therefore, the output electric signal delivered from ultrasonic transducer $R_s$ is decreased, causing a difference between the output electric signal delivered from ultrasonic transducer $R_s$ and that delivered from ultrasonic transducer $R_o$. The difference is detected by signal processing unit 3 and compared with that corresponding to a standard group of fibers or leaf fragments examined is evaluated. If signal processing unit 3 comprises a phase comparator to obtain an output electric signal detected in the form of phase comparison, a phase difference between the output electric signal delivered from ultrasonic transducer $R_s$ and that delivered from ultrasonic transducer $R_o$ is detected. Accordingly, a filling-density of the group of fibers or leaf fragments examined is evaluated by comparing the phase difference with that corresponding to a standard group of fibers or leaf fragments. When an output terminal of ultrasonic transducer $R_o$ is connected with input terminals of ultrasonic transducers $T_o$ and $T_s$ via amplifier 2, ultrasonic transducers $T_o$, $R_o$ and amplifier 2 form an oscillator with an ultrasonic propagation lane, as a delay element, between the cone center of ultrasonic transducer $T_o$ and that of ultrasonic transducer R. The oscillator enables the system for ultrasound transmission in materials in FIG. 1 to have a small-sized circuit with a simple structure. The small-sized circuit causes the system for ultrasound transmission in materials to have a small size which is very light in weight, and to be operated under low power consumption and low voltage.

Figure 4:
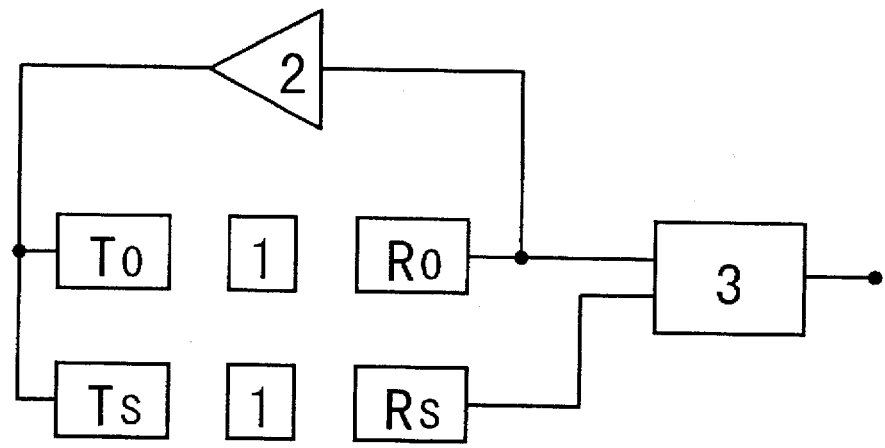
FIG. 4 shows a diagram of a driving circuit in case that another case 1 is placed between ultrasonic transducers $T_o$ and $R_o$ in the driving circuit in FIG. 3.

FIG. 4 shows a diagram of a driving circuit in case that another case 1 is placed between ultrasonic transducers $T_o$ and $R_o$ in the driving circuit in FIG. 3. When an examination group of fibers or leaf fragments is placed in case 1 between ultrasonic transducers $T_o$ and $R_s$, and a standard group of fibers or leaf fragments is placed in case 1 between ultrasonic transducers $T_o$ and $R_o$, a difference between the filling-densities of the examination group and the standard group is related to a difference between the output electric signals delivered from ultrasonic transducer $R_s$ and $R_o$.

Figure 5:
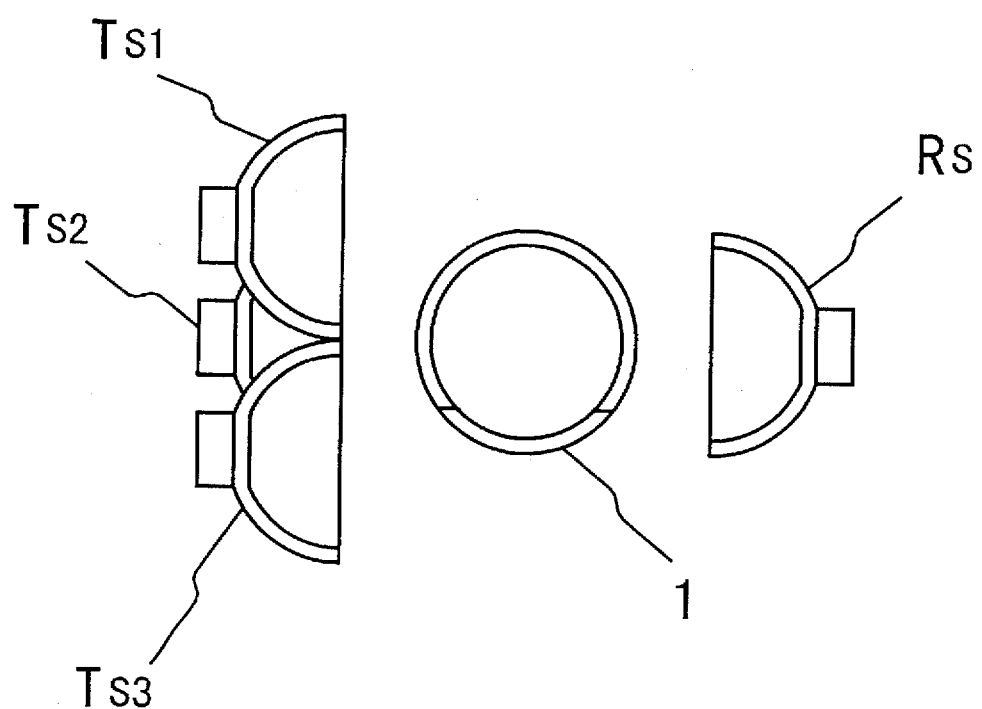
FIG. 5 shows a sectional view of the system for ultrasound transmission in materials according to a second embodiment of the present invention.

FIG. 5 shows a sectional view of a system for ultrasound transmission in materials according to a second embodiment of the present invention. The system for ultrasound transmission in materials comprises ultrasonic transducers $T_{o1}$, $T_{o2}$, $T_{o3}$, $T_{s1}$, $T_{s2}$, $T_{s3}$, $R_o$, $R_s$, case 1 placed between ultrasonic transducers $T_{s1}$, $T_{s2}$, $T_{s3}$ and ultrasonic transducer $R_s$, amplifier 2 and signal processing unit 3 comprising a differential amplifier. FIG. 5 shows only ultrasonic transducers $T_{s1}$, $T_{s2}$, $T_{s3}$, $R_s$ and case 1. Ultrasonic transducers $T_o$, $T_{o2}$, $T_{o3}$, $T_{s1}$, $T_{s2}$ and $T_{s3}$ are made from the same material as ultrasonic transducer $T_o$, and have the same cone construction having the center frequency of 39.2 kHz and the cone diameter of 1 cm. Three gravity centers of ultrasonic transducers $T_{o1}$, $T_{o2}$ and $T_{o3}$ make a triangle, and ultrasonic transducer $R_o$ is opposed to the center of the triangle, the distance between ultrasonic transducers $T_{o1}$, $T_{o2}$, $T_{o3}$ and ultrasonic transducer $R_s$ being 4.95 cm. Three gravity centers of ultrasonic transducers $T_{s1}$, $T_{s2}$ and $T_{s3}$ make a triangle, and ultrasonic transducer $R_s$ is opposed to the center of the triangle, the distance between ultrasonic transducers $T_{s1}$, $T_{s2}$, $T_{s3}$ and ultrasonic transducer $R_s$ being 4.95 cm. The relative position of ultrasonic transducers $T_{o1}$, $T_{o2}$ and $T_{o3}$ to ultrasonic transducer $R_o$ is equal to that of ultrasonic transducers $T_{s1}$, $T_{s2}$ and $T_{s3}$ to ultrasonic transducer $R_s$. Case 1 is not always placed between ultrasonic transducers $T_{o1}$, $T_{o2}$, $T_{o3}$ and ultrasonic transducer $R_o$.

Figure 6:
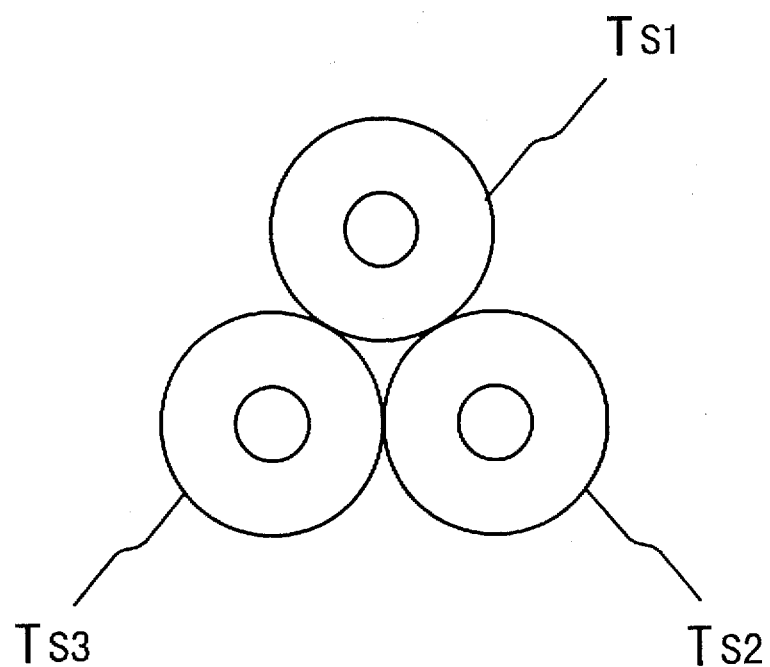
FIG. 6 shows a plan view of ultrasonic transducers $T_{s1}$, $T_{s2}$ and $T_{s3}$ viewed from case 1.

FIG. 6 shows a plan view of ultrasonic transducers $T_{s1}$, $T_{s2}$ and $T_{s3}$ viewed from case 1.

Figure 7:
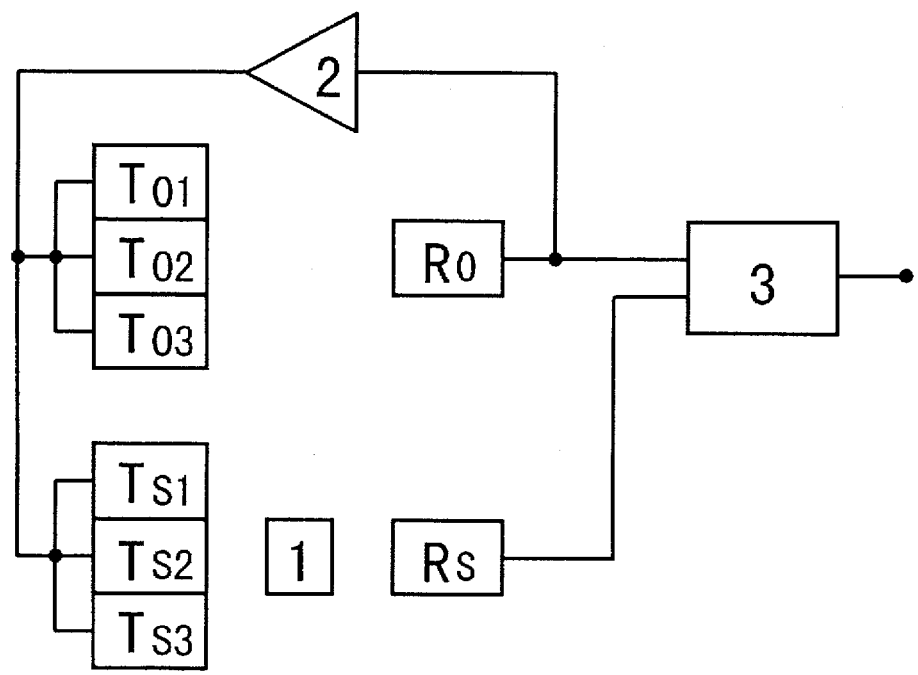
FIG. 7 shows a diagram of a driving circuit of the system for ultrasound transmission in materials in FIG. 5.

FIG. 7 shows a diagram of a driving circuit of the system for ultrasound transmission in materials in FIG. 5. Signal processing unit 3 is connected with output terminals of ultrasonic transducers $R_o$ and $R_s$. When operating the system for ultrasound transmission in materials in FIG. 5, electric signals are applied to ultrasonic transducers $T_{o1}$, $T_{o2}$ and $T_{o3}$, respectively. In this time, an ultrasound with a sharp directionality is emitted in air from the center of the triangle made by ultrasonic transducers $T_{o1}$, $T_{o2}$ and $T_{o3}$. The ultrasound is received by ultrasonic transducer $R_o$, and is delivered as an output electric signal from ultrasonic transducer $R_o$. In the same way, when electric signals are applied to ultrasonic transducers $T_{s1}$, $T_{s2}$ and $T_{s3}$, respectively, an ultrasound with a sharp directionality is emitted in air from the center of the triangle made by ultrasonic transducers $T_{s1}$, $T_{s2}$ and $T_{s3}$, and is received by ultrasonic transducer $R_s$ and delivered as an output electric signal from ultrasonic transducer $R_s$. Case 1 is placed at the area where the ultrasound emitted from ultrasonic transducers $T_{s1}$, $T_{s2}$ and $T_{s3}$ is most sharply and most strongly. If a group of fibers or leaf fragments wrapped in paper or others is placed in case 1, the ultrasound emitted from ultrasonic transducers $T_{s1}$, $T_{s2}$ and $T_{s3}$ goes through the group of fibers or leaf fragments. Therefore, the output electric signal delivered from ultrasonic transducer $R_s$ is decreased, causing a difference between the output electric signal delivered from ultrasonic transducer $R_s$ and that delivered from ultrasonic transducer $R_o$. The difference is detected by signal processing unit 3 and compared with that corresponding to a standard group of fibers or leaf fragments. Thus, a filling-density of the group of fibers or leaf fragments examined is evaluated. If signal processing unit 3 comprises a phase comparator, a phase difference between the output electric signals delivered from ultrasonic transducers $R_s$ and $R_o$ is detected. Accordingly, a filling-density of the group of fibers or leaf fragments examined is evaluated by comparing the phase difference with that corresponding to a standard group of fibers or leaf fragments. The system for ultrasound transmission in materials in FIG. 5 enables a higher sensitive operation under a low voltage in comparison with that in FIG. 1, owing to input ultrasonic transducers emitting an ultrasound with a sharp directionality. An output terminal of ultrasonic transducer $R_o$ is connected with input terminals of ultrasonic transducers $T_{o1}$, $T_{o2}$, $T_{o3}$, $T_{s1}$, $T_{s2}$ and $T_{s3}$ via amplifier 2. Thus, ultrasonic transducers $T_{o1}$, $T_{o2}$, $T_{o3}$, $R_o$ and amplifier 2 form an oscillator with an ultrasonic propagation lane, as a delay element, between the center of the triangle made by ultrasonic transducers $T_{o1}$, $T_{o2}$ and $T_{o3}$, and the cone center of ultrasonic transducer $R_o$. The oscillator enables the system for ultrasound transmission in materials in FIG. 5 to have a small-sized circuit with a simple structure. The small-sized circuit causes the system for ultrasound transmission in materials to have a small size which is very light in weight, and to be operated under low power consumption and low voltage. If another case 1 is placed between ultrasonic transducers $T_{o1}$, $T_{o2}$, $T_{o3}$ and ultrasonic transducer $R_o$ in the driving circuit in FIG. 7, an examination group of fibers or leaf fragments can be placed in case I between ultrasonic transducers $T_{s1}$, $T_{s2}$, $T_{s3}$, and ultrasonic transducer $R_s$, and a standard group of fibers or leaf fragments can be placed in case 1 between ultrasonic transducers $T_{o1}$, $T_{o2}$, $T_{o3}$ and ultrasonic transducer $R_o$. In this time, a difference between the filling-densities of the examination group and the standard group is related to a difference between the output electric signals delivered from ultrasonic transducer $R_s$ and $R_o$.

Figure 8:
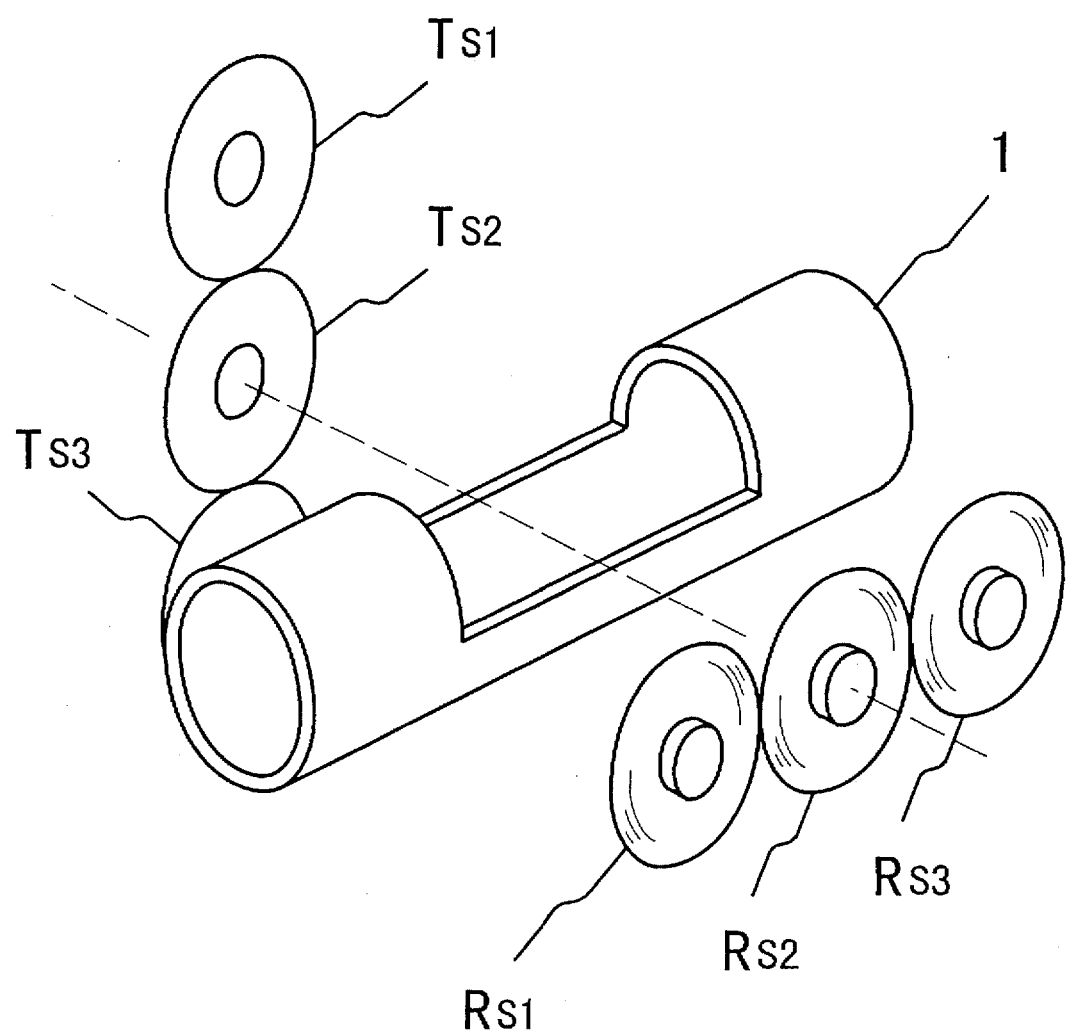
FIG. 8 shows a perspective view of the system for ultrasound transmission in materials according to a third embodiment of the present invention.

FIG. 8 shows a perspective view of a system for ultrasound transmission in materials according to a third embodiment of the present invention. The system for ultrasound transmission in materials comprises ultrasonic transducers $T_{o1}$, $T_{o2}$, $T_{o3}$, $T_{s1}$, $T_{s2}$, $T_{s3}$, $R_{o1}$, $R_{o2}$, $R_{o3}$, $R_{s1}$, $R_{s2}$, $R_{s3}$, case 1, amplifier 2 and signal processing unit 3 comprising a differential amplifier. Case 1 is placed between ultrasonic transducers $T_{s1}$, $T_{s2}$ and $T_{s3}$, and ultrasonic transducers $R_{s1}$, $R_{s2}$ and $R_{s3}$. FIG. 8 shows only ultrasonic transducers $T_{s1}$, $T_{s2}$, $T_{s3}$, $R_{s1}$, $R_{s2}$, $R_{s3}$ and case 1. Ultrasonic transducers $R_{o1}$, $R_{o2}$, $R_{o3}$, $R_{s1}$, $R_{s2}$ and $R_{s3}$ are made from the same material as ultrasonic transducer $T_o$, and have the same cone construction having the center frequency of 39.2 kHz and the cone diameter of 1 cm. Ultrasonic transducers $T_{o1}$, $T_{o2}$ and $T_{o3}$ are arranged such that three gravity centers thereof make a straight line, and ultrasonic transducers $R_{o1}$, $R_{o2}$, $T_{o3}$ are arranged such that three gravity centers thereof make a straight line. The straight line made by ultrasonic transducers $T_{o1}$, $T_{o2}$ and $T_{o3}$ is vertical to the straight line made by ultrasonic transducers $R_{o1}$, $R_{o2}$ and $R_{o3}$, the distance between ultrasonic transducers $T_{o1}$, $T_{o2}$, $T_{o3}$ and ultrasonic transducers $R_{o1}$, $R_{o2}$, $R_{o3}$ being 4.95 cm. Ultrasonic transducers $T_{s1}$, $T_{s2}$ and $T_{s3}$ are arranged such that three gravity centers thereof make a straight line, and ultrasonic transducers $R_{s1}$, $R_{s2}$ and $R_{s3}$ are arranged such that three gravity centers thereof make a straight line. The straight line made by ultrasonic transducers $T_{s1}$, $T_{s2}$ and $T_{s3}$ is vertical to the straight line made by ultrasonic transducers $R_{s1}$, $R_{s2}$ and $R_{s3}$ the distance between ultrasonic transducers $T_{s1}$, $T_{s2}$, $T_{s3}$ and ultrasonic transducers $R_{s1}$, $R_{s2}$, $R_{s3}$ being 4.95 cm. The relative position of ultrasonic transducers $T_{o1}$, $T_{o2}$ and $T_{o3}$ to ultrasonic transducers $R_{o1}$, $R_{o2}$ and $R_{o3}$ is equal to that of ultrasonic transducers $T_{s1}$, $T_{s2}$ and $T_{s3}$ to ultrasonic transducers $R_{s1}$, $R_{s2}$ and $R_{s3}$. Case 1 is not always placed between ultrasonic transducers $T_{o1}$, $T_{o2}$, $T_{o3}$ and ultrasonic transducers $R_{o1}$, $R_{o2}$, $R_{o3}$. In FIG. 8, three input ultrasonic transducers and three output ultrasonic transducers are used for ultrasound transmission. However, the numbers of the input and output ultrasonic transducers are not always three. If the numbers of the input and output ultrasonic transducers are five, five ultrasonic transducerts $T_{o1}$, $T_{o2}$, $T_{o3}$, $T_{o4}$ and $T_{o5}$ arranged such that five gravity centers thereof make a straight line are used in place of ultrasonic transducers $T_{o1}$, $T_{o2}$ and $T_{o3}$, five ultrasonic transducers $R_{o1}$, $R_{o2}$, $R_{o3}$, $R_{o4}$ and $R_{o5}$ arranged such that five gravity centers thereof make a straight line are used in place of ultrasonic transducers $R_{o1}$, $R_{o2}$ and $R_{o3}$, five ultrasonic transducers $T_{s1}$, $T_{s2}$, $T_{s3}$, $T_{s4}$ and $T_{s5}$ arranged such that five gravity centers thereof make a straight line are used in place of ultrasonic transducers $T_{s1}$, $T_{s2}$ and $T_{s3}$, and five ultrasonic transducers $R_{s1}$, $R_{s2}$, $R_{s3}$, $R_{s4}$ and $R_{s5}$ arranged such that five gravity centers thereof make a straight line are used in place of ultrasonic transducers $R_{s1}$, $R_{s2}$, $R_{s3}$. In this time, ultrasonic transducers $T_{o4}$, $T_{o5}$, $R_{o4}$, $R_{o5}$, $T_{s4}$, $T_{s5}$, $R_{s4}$ and $R_{s5}$ are made from the same material as ultrasonic transducer $T_o$, and have the same cone construction. The straight line made by ultrasonic transducers $T_{o1}$, $T_{o2}$, $T_{o3}$, $T_{o4}$ and $T_{o5}$ is vertical to the straight line made by ultrasonic transducers $R_{o1}$, $R_{o2}$, $R_{o3}$, $R_{o4}$ and $R_{o5}$. The straight line made by ultrasonic transducers $T_{s1}$, $T_{s2}T_{s3}$, $T_{s4}$ and $T_{s5}$ is vertical to the straight line made by ultrasonic transducers $R_{s1}$, $R_{s2}$, $R_{s3}$, $R_{s4}$ and $R_{s5}$.

Figure 9:
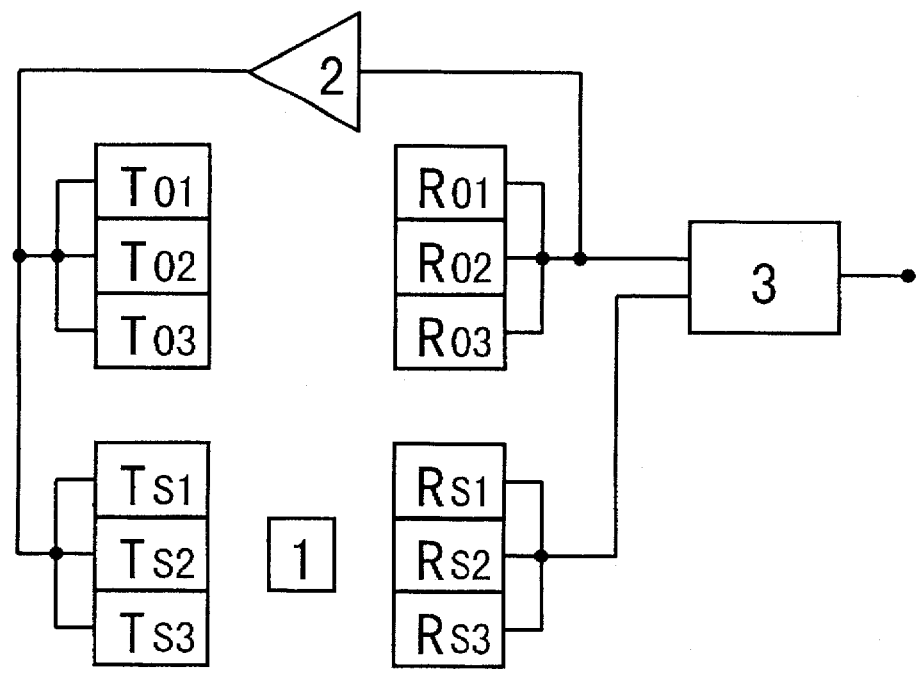
FIG. 9 shows a diagram of a driving circuit of the system for ultrasound transmission in materials in FIG. 8.

FIG. 9 shows a diagram of a driving circuit of the system for ultrasound transmission in materials in FIG. 8. Signal processing unit 3 is connected with a point linking three output terminals of ultrasonic transducers $R_{o1}$, $R_{o2}$ and $R_{o3}$, and a point linking three output terminals of ultrasonic transducers $R_{s1}$, $R_{s2}$ and $R_{s3}$. When operating the system for ultrasound transmission in materials in FIG. 8, electric signals are applied to ultrasonic transducers $T_{o1}$, $T_{o2}$ and $T_{o3}$, respectively, then an ultrasound with a sharp directionality is emitted in air from the center of the straight line made by ultrasonic transducers $T_{o1}$, $T_{o2}$ and $T_{o3}$. The ultrasound is received by ultrasonic transducers $R_{o1}$, $R_{o2}$ and $R_{o3}$, and is delivered as output electric signals from ultrasonic transducers $R_{o1}$, $R_{o2}$ and $R_{o3}$, respectively. In this time, ultrasonic transducers $T_{o1}$, $T_{o2}$ and $T_{o3}$ has an ability to emit an ultrasound with a directionality on a surface including three gravity centers of ultrasonic transducers $T_{o1}$, $T_{o3}$ and $R_{o2}$, and ultrasonic transducers $R_{o1}$, $R_{o2}$ and $R_{o3}$ has an ability to receive an ultrasound with a directionality on a surface including three gravity centers of ultrasonic transducers $T_{o2}$, $R_{o1}$ and $R_{o3}$. In the same way, when electric signals are applied to ultrasonic transducers $T_{s1}$, $T_{s2}$ and $T_{s3}$, respectively, an ultrasound with a sharp directionality is emitted in air from the center of the straight line made by ultrasonic transducers $T_{s1}$, $T_{s2}$ and $T_{s3}$, the ultrasound being received by ultrasonic transducers $R_{s1}$, $R_{s2}$ and $R_{s3}$, and delivered as output electric signals from ultrasonic transducers $R_{s1}$, $R_{s2}$ and $R_{s3}$, respectively. In this time, ultrasonic transducers $T_{s1}$, $T_{s2}$ and $T_{s3}$ has an ability to emit an ultrasound with a directionality on a surface including three gravity centers of ultrasonic transducers $T_{s1}$, $T_{s3}$ and $R_{s2}$, and ultrasonic transducers $R_{s1}$, $RS_{s2}$ and $R_{s3}$ has an ability to receive an ultrasound with a directionality on a surface including three gravity centers of ultrasonic transducers $T_{s2}$, $R_{s1}$ and $R_{s3}$. Case 1 is placed at the area where the ultrasound emitted from ultrasonic transducers $T_{s1}$, $T_{s2}$ and $T_{s3}$ is most sharply and most strongly. If a group of fibers or leaf fragments wrapped in paper or others is placed in case 1, the ultrasound emitted from ultrasonic transducers $T_{s1}$, $T_{s2}$ and $T_{s3}$ goes through the group of fibers or leaf fragments. Therefore, an output electric signal delivered from the point linking output terminals of ultrasonic transducers $R_{s1}$, $R_{s2}$ and $R_{s3}$ decreased, causing a difference between the output electric signal delivered from the point linking output terminals of ultrasonic transducers $R_{s1}$, $R_{s2}$, $R_{s3}$ and that delivered from the point linking output terminals of ultrasonic transducers $R_{o1}$, $R_{o2}$ and $R_{o3}$. The difference is detected by signal processing unit 3 and compared with that corresponding to a standard group of fibers or leaf fragments. Thus, a filling-density of the group of fibers or leaf fragments examined is evaluated. If signal processing unit 3 comprises a phase comparator, a phase difference between the output electric signal delivered from the point linking output terminals of ultrasonic transducers $R_{s1}$, $R_{s2}$, $R_{s3}$ and that delivered from the point linking output terminals of ultrasonic transducers $R_{o1}$, $R_{o2}$, $R_{o3}$ is detected. Accordingly, a filling-density of the group of fibers or leaf fragments examined is evaluated by comparing the phase difference with that corresponding to a standard group of fibers or leaf fragments. The system for ultrasound transmission in materials in FIG. 8 enables a higher sensitive operation under a low voltage in comparison with that in FIG. 1, because of input ultrasonic transducers emitting an ultrasound with a sharp directionality, and output ultrasonic transducers receiving an ultrasound with a sharp directionality. The point linking output terminals of ultrasonic transducers $R_{o1}$, $R_{o2}$ and $R_{o3}$ is connected with input terminals of ultrasonic transducers $T_{o1}$, $T_{o2}$, $T_{o3}$, $T_{s1}$, $T_{s2}$ and $T_{s3}$ via amplifier 2. Thus, ultrasonic transducers $T_{o1}$, $T_{o2}$, $T_{o3}$, $R_{o1}$, $R_{o2}$, $R_{o3}$ and amplifier 2 form an oscillator with an ultrasonic propagation lane, as a delay element, between the center of the straight line made by ultrasonic transducers $T_{o1}$, $T_{o2}$ and $T_{o3}$, and the center of the straight line made by ultrasonic transducers $R_{o1}$, $R_{o2}$ and $R_{o3}$. The oscillator enables the system for ultrasound transmission in materials in FIG. 8 to have a small-sized circuit with a simple structure. The small-sized circuit causes the system for ultrasound transmission in materials to have a small size which is very light in weight, and to be operated under low power consumption and low voltage. If another case 1 is placed between ultrasonic transducers $T_{o1}$, $T_{o2}$, $T_{o3}$ and ultrasonic transducers $R_{o1}$, $R_{o2}$ and $R_3$ in the driving circuit in FIG. 9, an examination group of fibers or leaf fragments can be placed in case 1 between ultrasonic transducers $T_{s1}$, $T_{s2}$, $T_{s3}$ and ultrasonic transducers $R_{s1}$, $R_{s2}$, $R_{s3}$, and a standard group of fibers or leaf fragments can be placed in case 1 between ultrasonic transducers $T_{o1}$, $T_{o2}$, $T_{o3}$ and ultrasonic transducers $R_{o1}$, $R_{o2}$, $R_{o3}$. In this time, a difference between the filling-densities of the examination group and the standard group is related to a difference between the output electric signal delivered from the point linking output terminals of ultrasonic transducers $R_{s1}$, $R_{s2}$, $R_{s3}$ and that delivered from the point linking output terminals of ultrasonic transducers $R_{o1}$, $R_{o2}$, $T_{o3}$.

Figure 10:
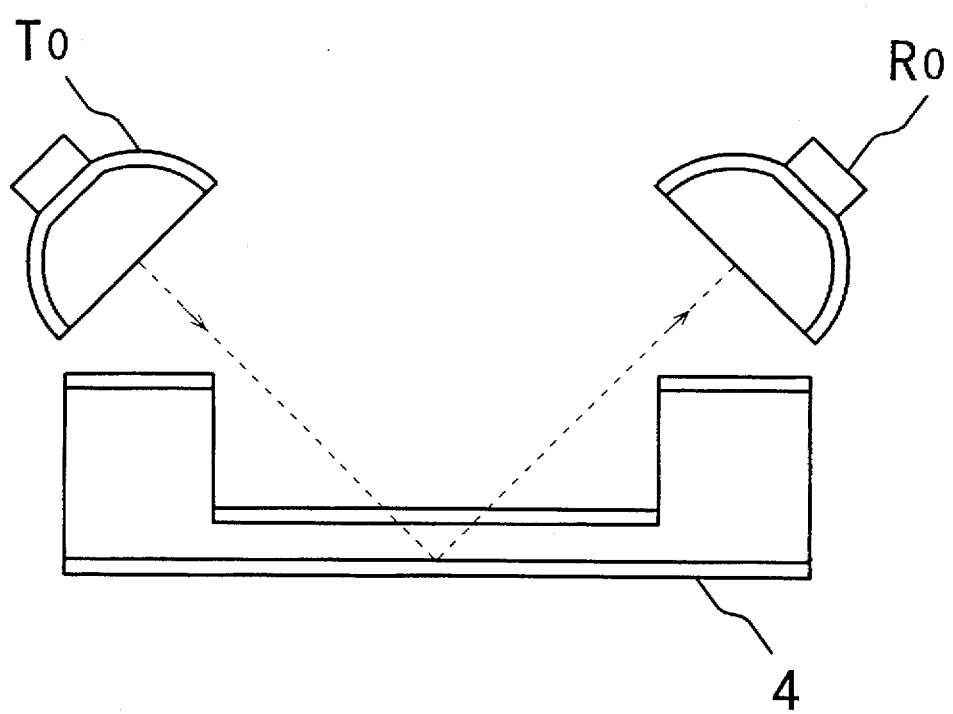
FIG. 10 shows a sectional view of the system for ultrasound transmission in materials according to a fourth embodiment of the present invention.

FIG. 10 shows a sectional view of a system for ultrasound transmission in materials according to a fourth embodiment of the present invention. The system for ultrasound transmission in materials comprises ultrasonic transducers $T_o$, $R_o$, $T_s$, $R_s$, amplifier 2, signal processing unit 3 comprising a differential amplifier, reference case 4 and examination case 5. FIG. 10 shows only ultrasonic transducers $T_o$, $R_o$ and reference case 4. Both reference case 4 and examination case 5 have the same structure as case 1, and are made of the same material as case 1. The relative position of ultrasonic transducers $T_s$ and $R_s$ to examination case 5 is equal to that of ultrasonic transducers $T_o$ and $R_o$ to reference case 4.

Figure 11:
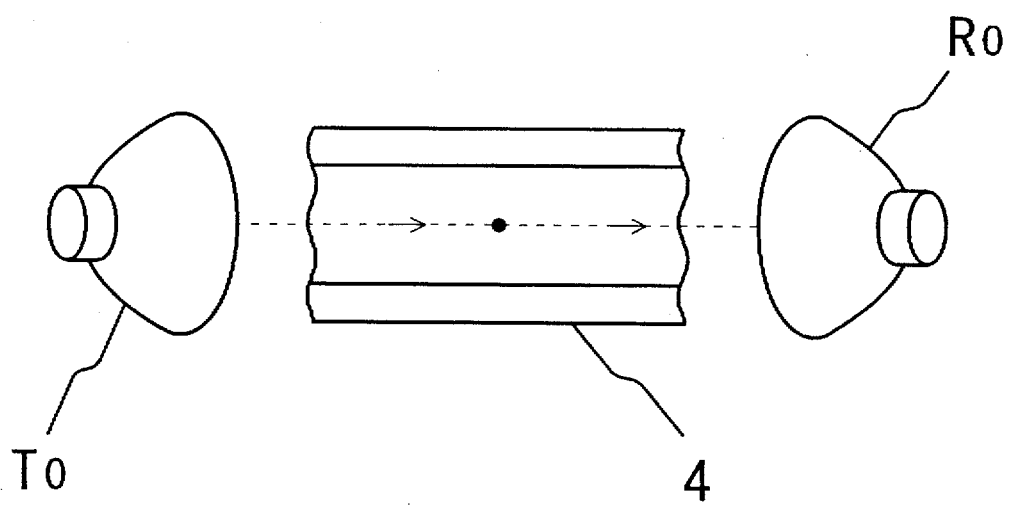
FIG. 11 shows a plan view of ultrasonic transducers $T_o$, $R_o$ and reference case 4 in FIG. 10 viewed from upside.

FIG. 11 shows a plan view of ultrasonic transducers $T_o$, $R_o$ and reference case 4 in FIG. 10 viewed from upside.

When operating the system for ultrasound transmission in materials in FIG. 10, a driving circuit having reference case 4 in place of case 1 between ultrasonic transducers $T_o$ and $R_o$, and having examination case 5 in place of case 1 between ultrasonic transducers $T_s$ and $R_s$ in FIG. 4 is employed. If an electric signal is applied to ultrasonic transducer $T_o$, an ultrasound is emitted in air from the cone center of ultrasonic transducer $T_o$. The ultrasound is reflected by a concavity at the bottom of reference case 4, and then received by ultrasonic transducer $R_o$, the ultrasound being delivered as an output electric signal from ultrasonic transducer $R_o$. In the same way, when an electric signal is applied to ultrasonic transducer $T_s$, an ultrasound is emitted in air from the cone center of ultrasonic transducer $T_s$, and is reflected by a concavity at the bottom of examination case 5, the ultrasound being received by ultrasonic transducer $R_s$ and delivered as an output electric signal from ultrasonic transducer $R_s$. If a group of fibers or leaf fragments wrapped in paper or others is placed on the concavity of examination case 5, the ultrasound emitted from ultrasonic transducer $T_s$ goes through the group of fibers or leaf fragments twice. Therefore, the output electric signal delivered from ultrasonic transducer $R_s$ is decreased, causing a difference between the output electric signals delivered from ultrasonic transducers $R_s$ and $R_o$. The difference is detected by signal processing unit 3 and compared with that corresponding to a standard group of fibers or leaf fragments. Thus, a filling-density of the group of fibers or leaf fragments examined is evaluated. If signal processing unit 3 comprises a phase comparator, a filling-density of the group of fibers or leaf fragments examined is evaluated by comparing the phase difference with that corresponding to a standard group of fibers or leaf fragments. When an examination group of fibers or leaf fragments and a standard group of fibers or leaf fragments are placed in examination case 5 and reference case 4, respectively, a difference between the filling-densities of the examination group and the standard group is related to a difference between the output electric signals delivered from ultrasonic transducer $R_s$ and $R_o$.

Figure 12:
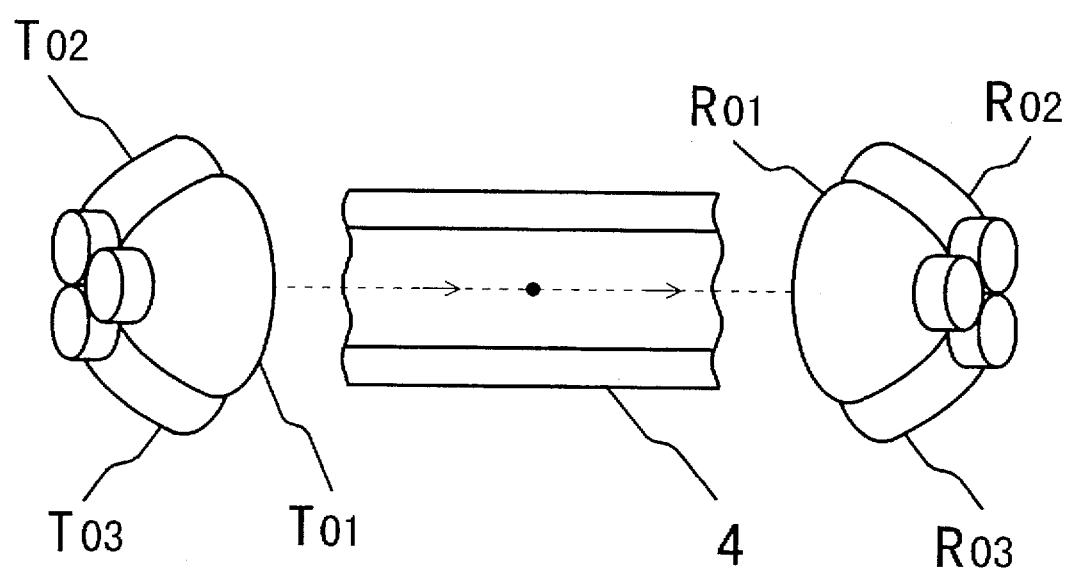
FIG. 12 shows a plan view of the system for ultrasound transmission in materials according to a fifth embodiment of the present invention.

FIG. 12 shows a plan view of a system for ultrasound transmission in materials according to a fifth embodiment of the present invention. The system for ultrasound transmission in materials comprises ultrasonic transducers $T_{o1}$, $T_{o2}$, $T_{o3}$, $T_{s1}$, $T_{s2}$, $T_{s3}$, $R_{o1}$, $R_{o2}$, $R_{o3}$, $R_{s1}$, $R_{s2}$, $R_{s3}$, amplifier 2, signal processing unit 3 comprising a differential amplifier, reference case 4 and examination case 5. FIG. 12 shows only ultrasonic transducers $T_{o1}$, $T_{o2}$, $T_{o3}$, $R_{o1}$, $R_{o2}$, $R_{o3}$, and reference case 4 viewed from upside. Three gravity centers of ultrasonic transducers $T_{o1}$, $T_{o2}$ and $T_{o3}$, three gravity centers of ultrasonic transducers $R_o$, $R_{o2}$ and $R_{o3}$ 3, three gravity centers of ultrasonic transducers $T_{s1}$, $T_{s2}$ and $T_{s3}$, and three gravity centers of ultrasonic transducers $R_{s1}$, $R_{s2}$ and $R_{s3}$ make triangles, respectively. The relative position of ultrasonic transducers $T_{s1}$, $T_{s2}$, $T_{s3}$, $R_{s1}$, $R_{s2}$ and $R_{s3}$ to examination case 5 is equal to that of ultrasonic transducers $T_{o1}$, $T_{o2}$, $T_{o3}$, $R_{o1}$, $R_{o2}$ and $R_{o3}$ to reference case 4.

When operating the system for ultrasound transmission in materials in FIG. 12, a driving circuit having reference case 4 between ultrasonic transducers $T_{o1}$, $T_{o2}$, $T_{o3}$ and ultrasonic transducers $R_{o1}$, $R_{o2}$ and $R_{o3}$ and having examination case 5 in place of case 1 between ultrasonic transducers $T_{s1}$, $T_{s2}$, $T_{s3}$ and ultrasonic transducers $R_{s1}$, $R_{s2}$ and $R_{s3}$ in FIG. 9 is employed. If electric signals are applied to ultrasonic transducers $T_{o1}$, $T_{o2}$ and $T_{o3}$, respectively, an ultrasound with a sharp directionality is emitted in air from the center of the triangle made by ultrasonic transducers $T_{o1}$, $T_{o2}$ and $T_{o3}$. The ultrasound is reflected by the concavity of reference case 4, and then received by ultrasonic transducers $R_{o1}$, $R_{o2}$ and $R_{o3}$, the ultrasound being delivered as an output electric signal from a point linking output terminals of ultrasonic transducers $R_{o1}$, $R_{o2}$ and $R_{o3}$. In this time, ultrasonic transducers $T_{o1}$, $T_{o2}$ and $T_{o3}$ has an ability to emit an ultrasound with a sharp directionality centered on the center of the triangle made by ultrasonic transducers $T_{o1}$, $T_{o2}$ and $T_{o3}$, and ultrasonic transducers $R_{o1}$, $R_{o2}$ and $R_{o3}$ has an ability to receive an ultrasound with a sharp directionality centered on the center of the triangle made by ultrasonic transducers $R_{o1}$, $R_{o2}$ and $R_{o3}$. Reference case 4 is placed at the area where the ultrasound emitted from ultrasonic transducers $T_{o1}$, $T_{o2}$ and $T_{o3}$ is most sharply and most strongly. In the same way, when electric signals are applied to ultrasonic transducers $T_{s1}$, $T_{s2}$ and $T_{s3}$, respectively, an ultrasound with a sharp directionality is emitted in air from the center of the triangle made by ultrasonic transducers $T_{s1}$, $T_{s2}$ and $T_{s3}$. The ultrasound is reflected by the concavity of examination case 5, and then received by ultrasonic transducers $R_{s1}$, $R_{s2}$ and $R_{s3}$, the ultrasound being delivered as an output electric signal from a point linking output terminals of ultrasonic transducers $R_{s1}$, $R_{s2}$ and $R_{s3}$. In this time, ultrasonic transducers $T_{s1}$, $T_{s2}$ and $T_{s3}$ has an ability to emit an ultrasound with a sharp directionality centered on the center of the triangle made by ultrasonic transducers $T_{s1}$, $T_{s2}$ and $T_{s3}$, and ultrasonic transducers $R_{s1}$, $R_{s2}$ and $R_{s3}$ an ability to receive an ultrasound with a sharp directionality centered on the center of the triangle made by ultrasonic transducers $R_{s1}$, $R_{s2}$ and $R_{s3}$. Examination case 5 is placed at the area where the ultrasound emitted from ultrasonic transducers $T_{s1}$, $T_{s2}$ and $T_{s3}$ is most sharply and most strongly. If a group of fibers or leaf fragments wrapped in paper or others is placed on the concavity of examination case 5, the ultrasound emitted from ultrasonic transducers $T_{s1}$, $T_{s2}$ and $T_{s3}$ goes through the group of fibers or leaf fragments twice. Therefore, the output electric signal delivered from the point linking output terminals of ultrasonic transducers $R_{s1}$, $R_{s2}$ and $R_{s3}$ is decreased, causing a difference between the output electric signal delivered from the point linking output terminals of ultrasonic transducers $R_{s1}$, $R_{s2}$ and $R_{s3}$ and that delivered from the point linking output terminals of ultrasonic transducers $R_{o1}$, $R_{o2}$ and $R_{o3}$. The difference is detected by signal processing unit 3 and compared with that corresponding to a standard group of fibers or leaf fragments. Thus, a filling-density of the group of fibers or leaf fragments examined is evaluated. If signal processing unit 3 comprises a phase comparator, a filling-density of the group of fibers or leaf fragments examined is evaluated by comparing the phase difference with that corresponding to a standard group of fibers or leaf fragments. The system for ultrasound transmission in materials in FIG. 12 enables a higher sensitive operation under a low voltage in comparison with that in FIG. 10, because of input ultrasonic transducers emitting an ultrasound with a sharp directionality, and output ultrasonic transducers receiving an ultrasound with a sharp directionality. When an examination group of fibers or leaf fragments and a standard group of fibers or leaf fragments are placed in examination case 5 and reference case 4, respectively, a difference between the filling-densities of the examination group and the standard group is related to a difference between the output electric signal delivered from the point linking output terminals of ultrasonic transducers $R_{s1}$, $R_{s2}$ and $R_{s3}$ and that delivered from the point linking output terminals of ultrasonic transducers $R_{o1}$, $R_{o2}$ and $R_{o3}$.

Figure 13:
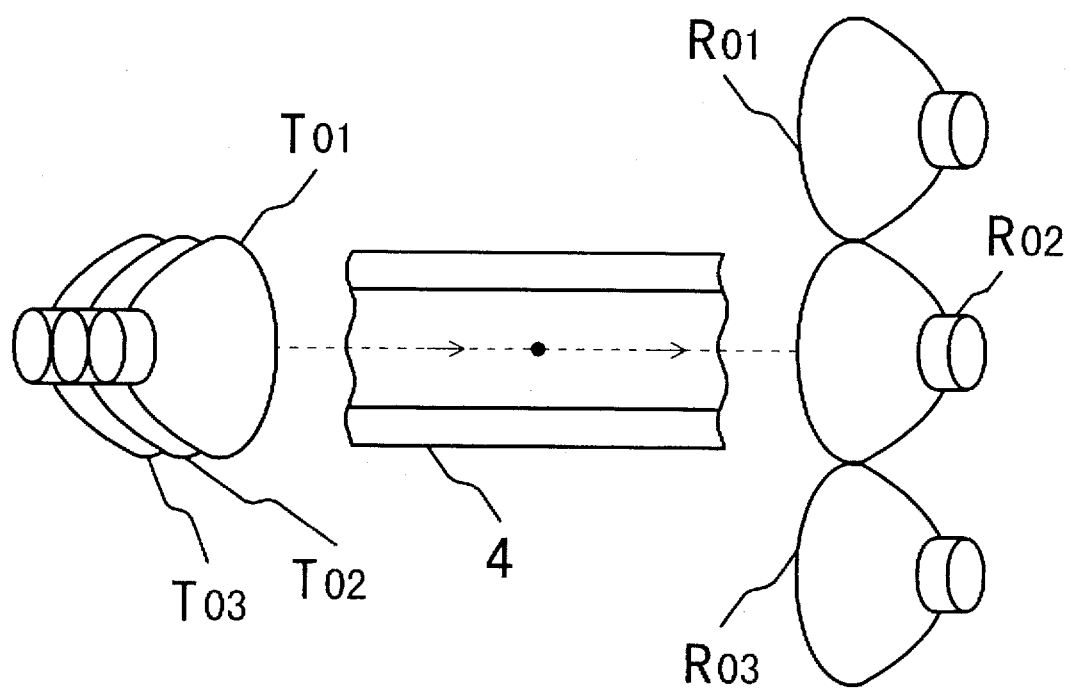
FIG. 13 shows a plan view of the system for ultrasound transmission in materials according to a sixth embodiment of the present invention.

FIG. 13 shows a plan view of a system for ultrasound transmission in materials according to a sixth embodiment of the present invention. The system for ultrasound transmission in materials comprises ultrasonic transducers $T_{o1}$, $T_{o2}$, $T_{o3}$, $T_{s1}$, $T_{s2}$, $T_{s3}$, $R_{o1}$, $R_{o2}$, $R_{o3}$, $R_{s1}$, $R_{s2}$, $R_{s3}$, amplifier 2, signal processing unit 3 comprising a differential amplifier, reference case 4 and examination case 5. FIG. 13 shows only ultrasonic transducers $T_{o1}$, $T_{o2}$, $T_{o3}$, $R_{o1}$, $R_{o2}$, $R_{o3}$ and reference case 4 viewed from upside. Ultrasonic transducers $T_{o1}$, $T_{o2}$ and $T_{o3}$ are arranged such that three gravity centers thereof make a straight line, and ultrasonic transducers $R_{o1}$, $R_{o2}$, $R_{o3}$ are arranged such that three gravity centers thereof make a straight line. The straight line made by ultrasonic transducers $T_{o1}$, $T_{o2}$ and $T_{o3}$ is vertical to the straight line made by ultrasonic transducers $R_{o1}$, $R_{o2}$ and $R_{o3}$. Ultrasonic transducers $T_{s1}$, $T_{s2}$ and $T_{s3}$ are arranged such that three gravity centers thereof make a straight line, and ultrasonic transducers $R_{s1}$, $R_{s2}$ and $R_{s3}$ are arranged such that three gravity centers thereof make a straight line. The straight line made by ultrasonic transducers $T_{s1}$, $T_{s2}$ and $T_{s3}$ is vertical to the straight line made by ultrasonic transducers $R_{s1}$, $R_{s2}$ and $R_{s3}$. The relative position of ultrasonic transducers $T_{s1}$, $T_{s2}$, $T_{s3}$, $R_{s1}$, $R_{s2}$ and $R_{s3}$ to examination case 5 is equal to that of ultrasonic transducers $T_{o1}$, $T_{o2}$, $T_{o3}$, $R_{o1}$, $R_{o2}$, and $R_{o3}$ to reference case 4.

When operating the system for ultrasound transmission in materials in FIG. 13, a driving circuit having reference case 4 between ultrasonic transducers $T_{o1}$, $T_{o2}$, $T_{o3}$ and ultrasonic transducers $R_{o1}$, $R_{o2}$ and $R_{o3}$, and having examination case 5 in place of case 1 between ultrasonic transducers $T_{s1}$, $T_{s2}$, $T_{s3}$ and ultrasonic transducers $R_{s1}$, $R_{s2}$ and $R_{s3}$ in FIG. 9 is employed. If electric signals are applied to ultrasonic transducers $T_{o1}$, $T_{o2}$ and $T_{o3}$, respectively, an ultrasound with a sharp directionality is emitted in air from the center of the straight line made by ultrasonic transducers $T_{o1}$, $T_{o2}$, and $T_{o3}$. The ultrasound is reflected by the concavity of reference case 4, and then received by ultrasonic transducers $R_{o1}$, $R_{o2}$ and $R_{o3}$, the ultrasound being delivered as an output signal from a point linking output terminals of ultrasonic transducers $R_{o1}$, $R_{o2}$ and $R_{o3}$. In this time, ultrasonic transducers $T_{o1}$, $T_{o2}$ and $T_{o3}$ has an ability to emit an ultrasound with a directionality on a surface including the concavity of reference case 4 and two gravity centers of ultrasonic transducers $T_{o1}$, and $T_{o3}$, and ultrasonic transducers $R_{o1}$, $R_{o2}$ and $R_{o3}$ has an ability to receive an ultrasound with a directionality on a surface including the concavity of reference case 4 and two gravity centers of ultrasonic transducers $R_{o1}$ and $R_{o3}$. Reference case 4 is placed at the area where the ultrasound emitted from ultrasonic transducers $T_{o1}$, $T_{o2}$ and $T_{o3}$ is most sharply and most strongly. In the same way, when electric signals are applied to ultrasonic transducers $T_{s1}$, $T_{s2}$ and $T_{s3}$, respectively, an ultrasound with a sharp directionality is emitted in air from the center of the straight line made by ultrasonic transducers $T_{s1}$, $T_{s2}$ and $T_{s3}$. The ultrasound is reflected by the concavity of examination case 5, and then received by ultrasonic transducers $R_{s1}$, $R_{s2}$ and $R_{s3}$, the ultrasound being delivered as an output electric signal from a point linking output terminals of ultrasonic transducers $R_{s1}$, $R_{s2}$ and $R_{s3}$. In this time, ultrasonic transducers $T_{s1}$, $T_{s2}$ and $T_{s3}$ has an ability to emit an ultrasound with a directionality on a surface including the concavity of examination case 5 and two gravity centers of ultrasonic transducers $T_{s1}$, and $T_{s3}$, and ultrasonic transducers $R_{s1}$, $R_{s2}$ and $R_{s3}$ has an ability to receive an ultrasound with a directionality on a surface including the concavity of examination case 5 and two gravity centers of ultrasonic transducers $R_{s1}$, and $R_{s3}$. Examination case 5 is placed at the area where the ultrasound emitted from ultrasonic transducers $T_{s1}$, $T_{s2}$ and $T_{s3}$ is most sharply and most strongly. If a group of fibers or leaf fragments wrapped in paper or others is placed on the concavity of examination case 5, the ultrasound emitted from ultrasonic transducers $T_{s1}$, $T_{s2}$ and $T_{s3}$ goes through the group of fibers or leaf fragments twice. Therefore, the output electric signal delivered from the point linking output terminals of ultrasonic transducers $R_{s1}$, $R_{s2}$ and $R_{s3}$ is decreased, causing a difference between the output electric signal delivered from the point linking output terminals of ultrasonic transducers $R_{s1}$, $R_{s2}$ and $R_{s3}$ and that delivered from the point linking output terminals of ultrasonic transducers $R_{o1}$, $R_{o2}$ and $R_{o3}$. The difference is detected by signal processing unit 3 and compared with that corresponding to a standard group of fibers or leaf fragments. Thus, a filling-density of the group of fibers or leaf fragments examined is evaluated. If signal processing unit 3 comprises a phase comparator, a filling-density of the group of fibers or leaf fragments examined is evaluated by comparing the phase difference with that corresponding to a standard group of fibers or leaf fragments. The system for ultrasound transmission in materials in FIG. 13 enables a higher sensitive operation under a low voltage in comparison with that in FIG. 10, because of input ultrasonic transducers emitting an ultrasound with a sharp directionality, and output ultrasonic transducers receiving an ultrasound with a sharp directionality. When an examination group of fibers or leaf fragments and a standard group of fibers or leaf fragments are placed in examination case 5 and reference case 4, respectively, a difference between the filling-densities of the examination group and the standard group is related to a difference between the output electric signal delivered from the point linking output terminals of ultrasonic transducers $R_{s1}$, $R_{s2}$ and $R_{s3}$ and that delivered from the point linking output terminals of ultrasonic transducers $R_{o1}$, $R_{o2}$ and $R_{o3}$.

Figure 14:
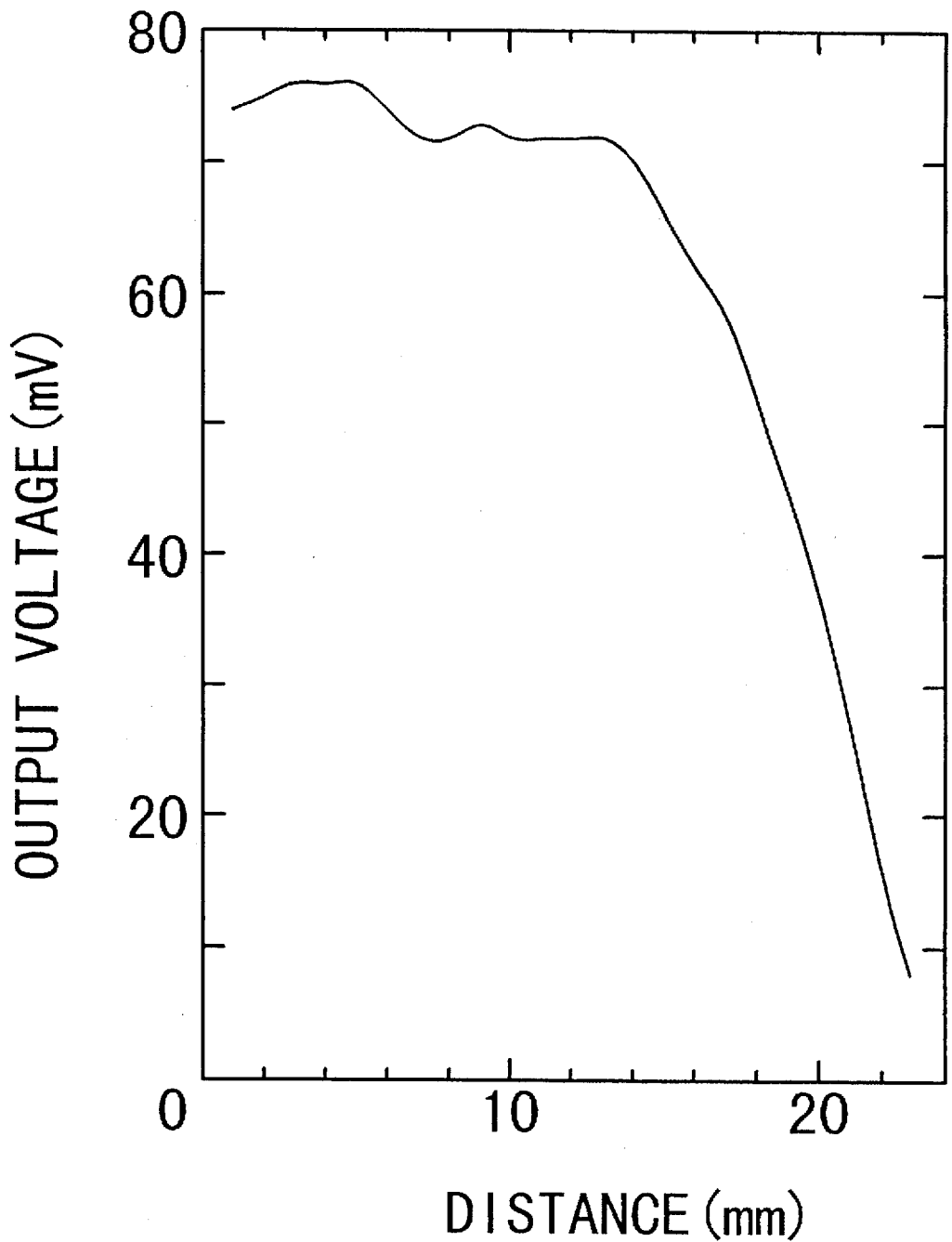
FIG. 14 shows a relationship between the output electric signal at ultrasonic transducer $R_s$ and the moving distance of ultrasonic transducer $R_s$ from the initial position to a position along a line including the initial position and vertical to the direction of the ultrasound emitted from ultrasonic transducer $T_s$ in FIG. 1.

FIG. 14 shows a relationship between the output electric signal at ultrasonic transducer $R_s$ and the moving distance of ultrasonic transducer $R_s$ from the initial position to a position along a line including the initial position and vertical to the direction of the ultrasound emitted from ultrasonic transducer $T_s$ in the system for ultrasound transmission in materials in FIG. 1. The moving distance is zero mm when ultrasonic transducer $R_s$ is right in front of ultrasonic transducer $T_s$ as in FIG. 1. An electric signal with 120 mV is applied to ultrasonic transducer $T_s$. It is clear from FIG. 14 that the ultrasound emitted from ultrasonic transducer $T_s$ is received by ultrasonic transducer $R_s$ effectively when the moving distance is under 14 mm. In other words, the ultrasound with the diameter under 28 mm goes through a group of fibers or leaf fragments effectively. Thus, case 1 has the opening at the top thereof, as shown in FIG. 2, for the purpose of ultrasound transmission.

Figure 15:
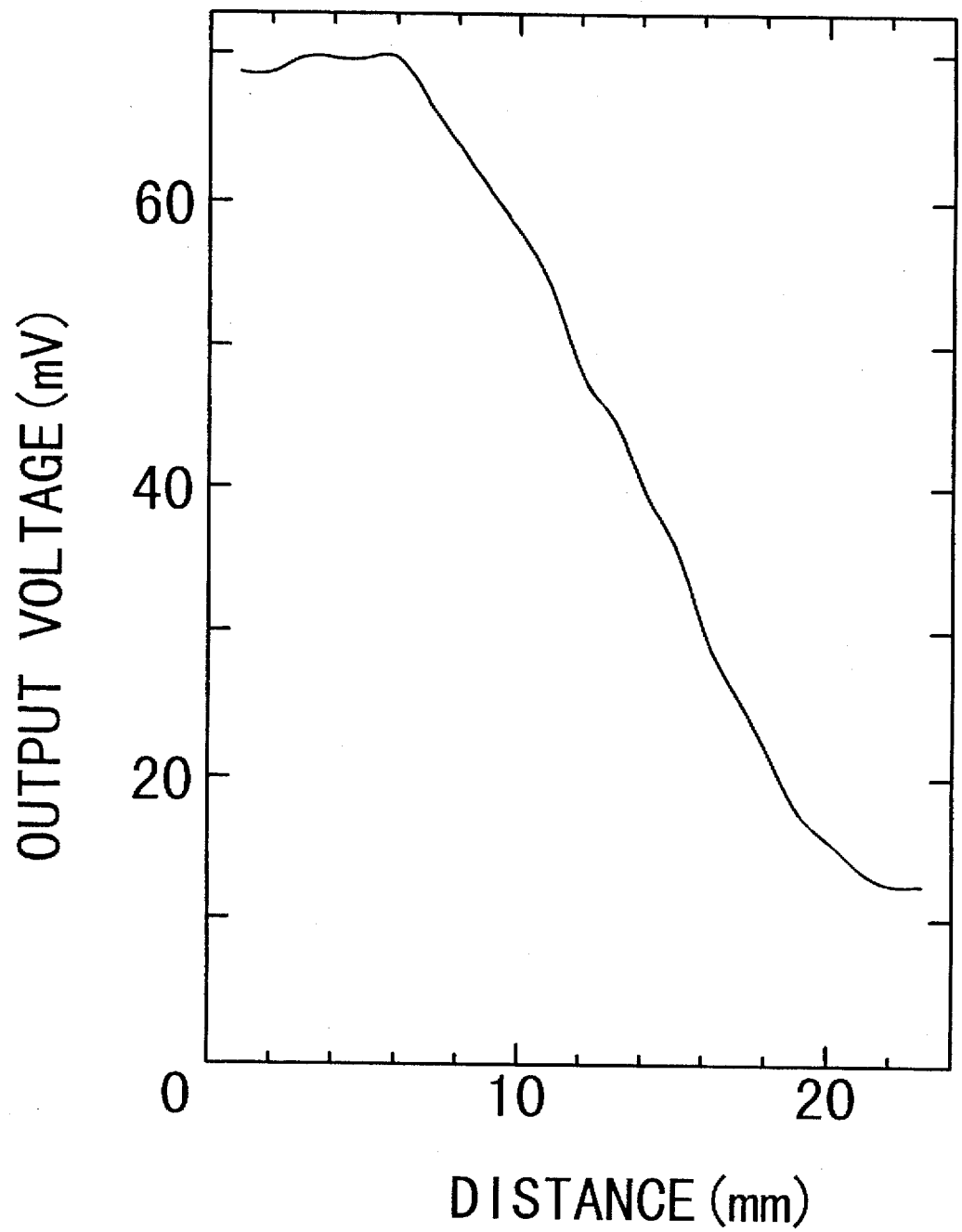
FIG. 15 shows a relationship between the output electric signal at ultrasonic transducer $R_s$ and the moving distance of ultrasonic transducer $R_s$ from the initial position to a position along a line including the initial position and vertical to the direction of the ultrasound emitted from ultrasonic transducers $T_{s1}$, $T_{s2}$ and $T_{s3}$ in FIG. 5.

FIG. 15 shows a relationship between the output electric signal at ultrasonic transducer $R_s$ and the moving distance of ultrasonic transducer $R_s$ from the initial position to a position along a line including the initial position and vertical to the direction of the ultrasound emitted from ultrasonic transducers $T_{s1}$, $T_{s2}$ and $T_{s3}$ in the system for ultrasound transmission in materials in FIG. 5. The moving distance is zero mm when ultrasonic transducer $R_s$ is right in front of the center of the triangle made by ultrasonic transducers $T_{o1}$, $T_{o2}$ and $T_{o3}$ as in FIG. 5. Electric signals with 40.8 mV are applied to ultrasonic transducers $T_{s1}$, $T_{s2}$ and $T_{s3}$, respectively. It is clear from FIG. 15 that the ultrasound emitted from ultrasonic transducers $T_{o1}$, $T_{o2}$ and $T_{o3}$ is received by ultrasonic transducer $R_s$ effectively when the moving distance is under 6 mm. In other words, the ultrasound with the diameter under 12 mm goes through a group of fibers or leaf fragments effectively. In addition, it is clear from FIGS. 14 and 15 that the ultrasound emitted from ultrasonic transducers $T_{o1}$, $T_{o2}$ and $T_{o3}$ in FIG. 5 has a sharp directionality in comparison with that emitted from ultrasonic transducer $T_s$ in FIG. 1.

Figure 16:
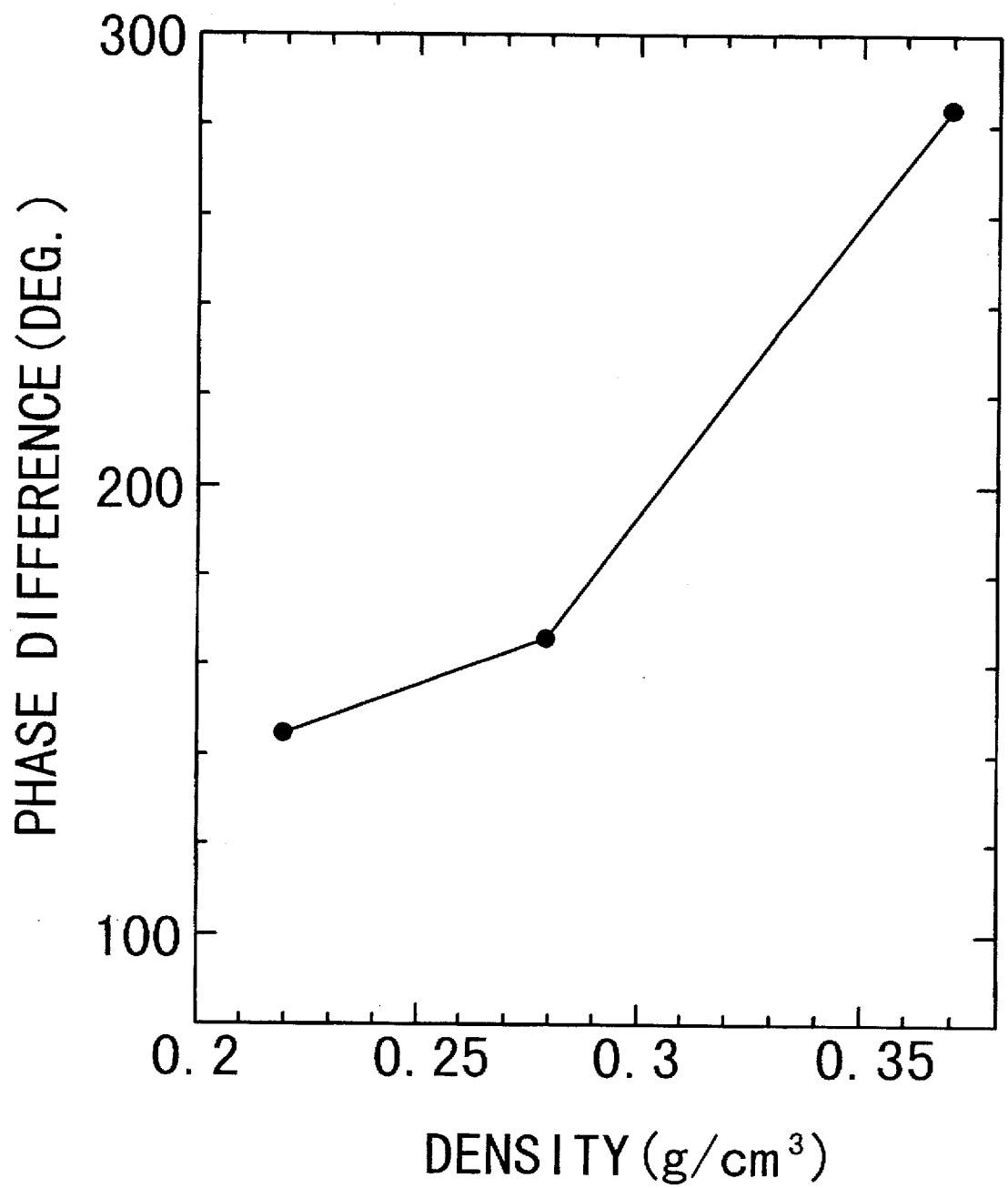
FIG. 16 shows a relationship between the output electric signal detected by signal processing unit 3 and a filling-density of a group of fibers or leaf fragments in case I of the system for ultrasound transmission in materials in FIG. 1.

FIG. 16 shows a relationship between the output electric signal detected by signal processing unit 3 and a filling density of a group of fibers or leaf fragments in case 1 of the system for ultrasound transmission in materials in FIG. 1. FIG. 16 shows a result in case that the distance between input and output ultrasonic transducers is 6.5 cm, in other words, both the distance between ultrasonic transducers $T_o$ and $R_o$, and the distance between ultrasonic transducers $T_s$ and $R_s$ are 6.5 cm. The output electric signal detected by signal processing unit 3 indicates a difference between the output electric signals delivered from ultrasonic transducer RS and R0. It is clear from FIG. 16 that the filling-density is related to the output electric signal detected by signal processing unit 3.

Figure 17:
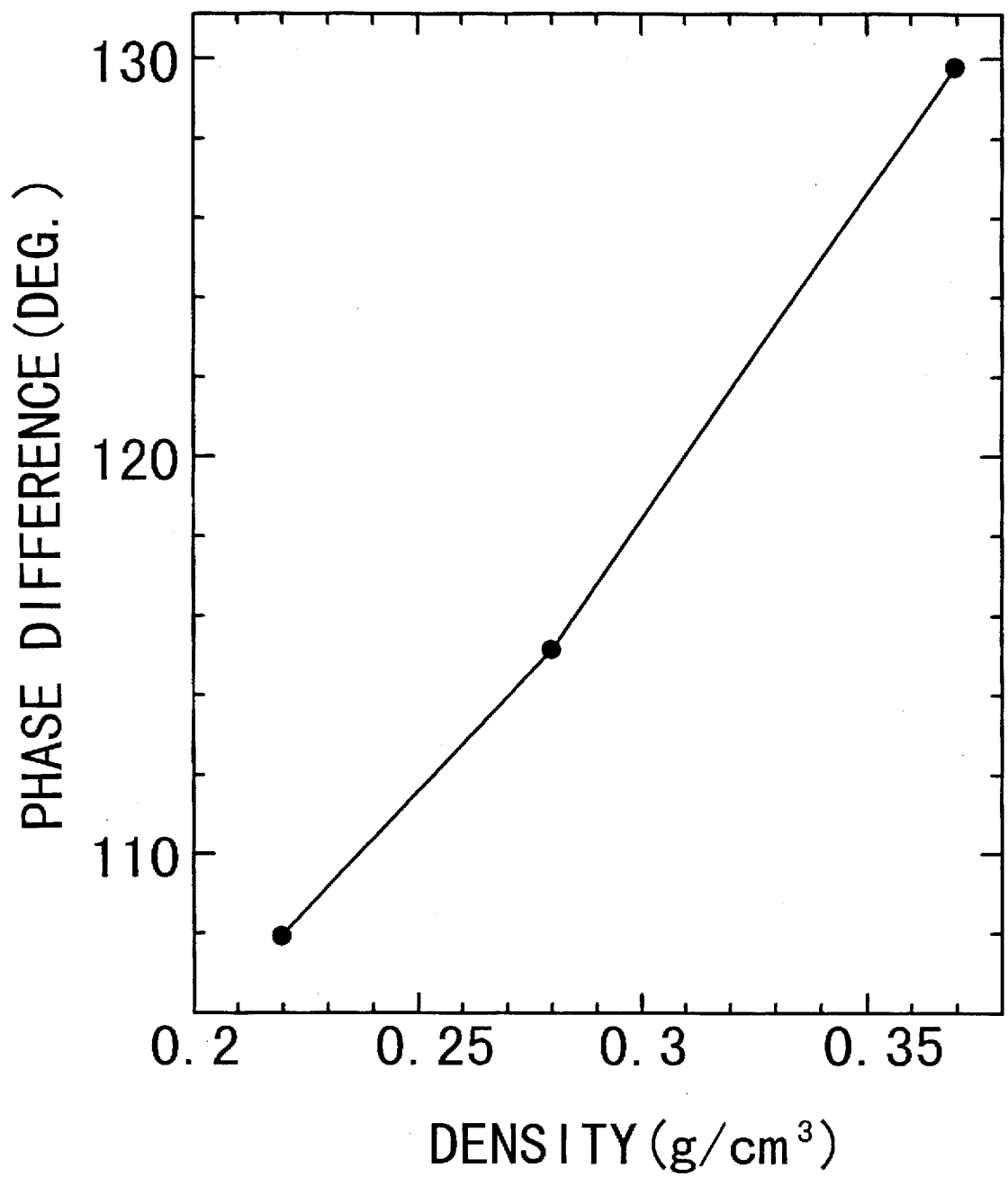
FIG. 17 shows a relationship between the output electric signal detected by signal processing unit 3 and a filling-density of a group of fibers or leaf fragments in case 1 of the system for ultrasound transmission in materials in FIG. 5.

FIG. 17 shows a relationship between the output electric signal detected by signal processing unit 3 and a filling density of a group of fibers or leaf fragments in case 1 of the system for ultrasound transmission in materials in FIG. 8. FIG. 17 shows a result in case that the numbers of the input and output ultrasonic transducers are five and the distance between input and output ultrasonic transducers is 6.5 cm, in other words, both the distance between ultrasonic transducers $T_{o1}$, $T_{o2}$, $T_{o3}$, $T_{o4}$, $T_{o5}$, and ultrasonic transducers $R_{o1}$, $R_{o2}$, $R_{o3}$, $T_{o4}$, $T_{o5}$ and the distance between ultrasonic transducers $T_{s1}$, $T_{s2}$, $T_{s3}$, $TS_{s4}$, $T_{s5}$, and ultrasonic transducers $R_{o1}$, $R_{o2}$, $R_{o3}$, $R_{s4}$, $R_{s5}$ are 6.5 cm. The output electric signal detected by signal processing unit 3 indicates a difference between the output electric signals delivered from the point linking output terminals of ultrasonic transducers $R_{s1}$, $R_{s2}$, $R_{s3}$, $R_{s4}$, and $R_{s5}$ and that delivered from the point linking output terminals of ultrasonic transducers $R_{o1}$, $R_{o2}$, $R_{o3}$, $R_{o4}$ and $R_{o5}$. It is clear from FIG. 17 that the filling-density is related to the output electric signal detected by signal processing unit 3. In addition, it is clear that the increasing rate of the output electric signal detected by signal processing unit 3 to the filling-density in FIG. 17 is more linear and more sensitive than that in FIG. 16. Therefore, the system for ultrasound transmission in materials in FIG. 8 has superior characteristics than that in FIG. 1.

While this invention has been described in connection with what is presently considered to be the most practical and preferred embodiment, it is to be understood that the invention is not limited to the disclosed embodiment, but, on the contrary, is intended to cover various modifications and equivalent arrangements included within the spirit and scope of the appended claims.

What is claimed is:

1. A system for ultrasound transmission in materials comprising:
    a reference unit consisting of
        at least an input ultrasonic transducer $T_o$ and
        at least an output ultrasonic transducer $R_o$ opposed to said ultrasonic transducer $T_o$;
    an examination unit consisting of
        at least an input ultrasonic transducer $T_s$ and
        at least an output ultrasonic transducer $R_s$ opposed to said ultrasonic transducer $T_s$;
    at least a case equipped in at least said examination unit, said case being placed between said ultrasonic transducers $T_s$ and $R_s$, and having an examination group of fibers or leaf fragments therein; and
    a signal processing unit connected with output terminals of said ultrasonic transducers $R_o$ and $R_s$;
        said ultrasonic transducer $T_o$ receiving an electric signal, transducing said electric signal to an ultrasound, and emitting said ultrasound in air,
        said ultrasonic transducer $R_o$ receiving said ultrasound emitted from said ultrasonic transducer $T_o$ and transducing said ultrasound to an output electric signal,
        said ultrasonic transducer $T_s$ receiving an electric signal, transducing said electric signal to an ultrasound, emitting said ultrasound in air, and making said ultrasound go through said examination group of fibers or leaf fragments,
        said ultrasonic transducer $R_s$ receiving said ultrasound transmitted through said examination group of fibers or leaf fragments, and transducing said ultrasound to an output electric signal.
        said signal processing unit detecting a difference between said output electric signals delivered from said ultrasonic transducers $R_o$ and $R_s$, comparing said difference with that corresponding to a standard group of fibers or leaf fragments, and evaluating a filling-density of said examination group of fibers or leaf fragments.

2. A system for ultrasound transmission in materials as defined in claim 1 further comprising an amplifier, an output terminal of said ultrasonic transducer $R_o$ being connected with input terminals of said ultrasonic transducers $T_o$ and $T_s$ via said amplifier, said ultrasonic transducers $T_o$, $R_o$ and said amplifier forming an oscillator with an ultrasonic propagation lane, as a delay element, between said ultrasonic transducers $T_o$ and $R_o$.

3. A system for ultrasound transmission in materials as defined in claim 1, wherein said signal processing unit comprising a phase comparator, said phase comparator detecting a phase difference between said output electric signals delivered from said ultrasonic transducers $R_o$ and $R_s$, comparing said phase difference with that corresponding to a standard group of fibers or leaf fragments, and evaluating a filling-density of said examination group of fibers or leaf fragments.

4. A system for ultrasound transmission in materials comprising:
    a reference unit consisting of
        three input ultrasonic transducers $T_{o1}$, $T_{o2}$ and $T_{o3}$, three gravity centers thereof making a triangle, and
        an output ultrasonic transducer $R_o$ opposed to the center of said triangle;
    an examination unit consisting of
        three input ultrasonic transducers $T_{s1}$, $T_{s2}$ and $T_{s3}$, three gravity centers thereof making a triangle, and an output ultrasonic transducer $R_s$ opposed to the center of said triangle;

at least a case equipped in at least said examination unit, said case being placed between said ultrasonic transducers $T_{s1}$, $T_{s2}$ and $T_{s3}$, and said ultrasonic transducer $R_s$, and having an examination group of fibers or leaf fragments therein; and a signal processing unit connected with output terminals of said ultrasonic transducers $R_o$ and $R_s$;

said ultrasonic transducers $T_{o1}$, $T_{o2}$ and $T_{o3}$ receiving electric signals, respectively, transducing said electric signals to an ultrasound with a sharp directionality, and emitting said ultrasound in air, said ultrasonic transducer $R_o$ receiving said ultrasound emitted from said ultrasonic transducers $T_{o1}$, $T_{o2}$ and $T_{o3}$, and transducing said ultrasound to an output electric signal, said ultrasonic transducers $T_{s1}$, $T_{s2}$ and $T_{s3}$ receiving electric signals, respectively, transducing said electric signals to an ultrasound with a sharp directionality, emitting said ultrasound in air, and making said ultrasound go through said examination group of fibers or leaf fragments, said case being placed at the area where said ultrasound emitted from said ultrasonic transducers $T_{s1}$, $T_{s2}$ and $T_{s3}$ is most sharply and most strongly, said ultrasonic transducer $R_s$ receiving said ultrasound transmitted through said examination group of fibers or leaf fragments, and transducing said ultrasound to an output electric signal, said signal processing unit detecting a difference between said output electric signals delivered from said ultrasonic transducers $R_o$ and $R_s$, comparing said difference with that corresponding to a standard group of fibers or leaf fragments, and evaluating a filling-density of said examination group of fibers or leaf fragments.

5. A system for ultrasound transmission in materials as defined in claim 4 further comprising an amplifier, an output terminal of said ultrasonic transducer $R_o$ being connected with input terminals of said ultrasonic transducers $T_{o1}$, $T_{o2}$, $T_{o3}$, $T_{s1}$, $T_{s2}$ and $T_{s3}$ via said amplifier, said ultrasonic transducers $T_{o1}$, $T_{o2}$, $T_{o3}$, $R_o$ and said amplifier forming an oscillator with an ultrasonic propagation lane, as a delay element, between said ultrasonic transducers $T_{o1}$, $T_{o2}$ and $T_{o3}$, and said ultrasonic transducer $R_o$.

6. A system for ultrasound transmission in materials as defined in claim 4, wherein said signal processing unit comprising a phase comparator, said phase comparator detecting a phase difference between said output electric signals delivered from said ultrasonic transducers $R_o$ and $R_s$, comparing said phase difference with that corresponding to a standard group of fibers or leaf fragments, and evaluating a filling-density of said examination group of fibers or leaf fragments.

7. A system for ultrasound transmission in materials comprising:

a reference unit consisting of at least two input ultrasonic transducers $T_{o1}$ and $T_{o2}$, and at least two output ultrasonic transducers $R_{o1}$ and $R_{o2}$, a straight line including two gravity centers of said ultrasonic transducers $T_{o1}$ and $T_{o2}$ being vertical to a straight line including two gravity centers of said ultrasonic transducers $R_{o1}$ and $R_{o2}$;

an examination unit consisting of at least two input ultrasonic transducers $T_{s1}$ and $T_{s2}$, and at least two output ultrasonic transducers $R_{s1}$ and $R_{s2}$, a straight line including two gravity centers of said ultrasonic transducers $T_{s1}$ and $T_{s2}$ being vertical to a straight line including two gravity centers of said ultrasonic transducers $R_{s1}$ and $R_{s2}$;

at least a case equipped in at least said examination unit, said case being placed between said ultrasonic transducers $T_{s1}$ and $T_{s2}$, and said ultrasonic transducer $R_{s1}$ and $R_{s2}$, and having an examination group of fibers or leaf fragments therein; and a signal processing unit connected with said point linking two output terminals of said ultrasonic transducers $R_{o1}$ and $R_{o2}$, and a point linking two output terminals of said ultrasonic transducers $R_{s1}$ and $R_{s2}$;

said ultrasonic transducers $T_{o1}$ and $T_{o2}$ receiving electric signals, respectively, transducing said electric signals to an ultrasound with a sharp directionality, and emitting said ultrasound in air, said ultrasonic transducers $R_{o1}$ and $R_{o2}$ receiving said ultrasound emitted from said ultrasonic transducers $T_{o1}$ and $T_{o2}$, and transducing said ultrasound to output electric signals, said ultrasonic transducers $T_{s1}$ and $T_{s2}$ receiving electric signals, respectively, transducing said electric signals to an ultrasound with a sharp directionality, emitting said ultrasound in air, and making said ultrasound go through said examination group of fibers or leaf fragments, said case being placed at the area where said ultrasound emitted from said ultrasonic transducers $T_{s1}$ and $T_{s2}$ is most sharply and most strongly, said ultrasonic transducers $R_{s1}$ and $R_{s2}$ receiving said ultrasound transmitted through said examination group of fibers or leaf fragments, and transducing said ultrasound to output electric signals, said signal processing unit detecting a difference between an output electric signal delivered from said point linking two output terminals of said ultrasonic transducers $R_{o1}$ and $R_{o2}$ and an output electric signal delivered from said point linking two output terminals of said ultrasonic transducers $R_{s1}$ and $R_{s2}$, comparing said difference with that corresponding to a standard group of fibers or leaf fragments, and evaluating a filling-density of said examination group of fibers or leaf fragments.

8. A system for ultrasound transmission in materials as defined in claim 7 further comprising an amplifier, a point linking two output terminals of said ultrasonic transducers $R_{o1}$ and $R_{o2}$ being connected with input terminals of said ultrasonic transducers $T_{o1}$, $T_{o2}$, $T_{s1}$ and $T_{s2}$ via said amplifier, said ultrasonic transducers $T_{o1}$, $T_{o2}$, $R_{o1}$, $R_{o2}$ and said amplifier forming an oscillator with an ultrasonic propagation lane, as a delay element, between said ultrasonic transducers $T_{o1}$ and $T_{o2}$, and said ultrasonic transducer $R_{o1}$ and $R_{o2}$.

9. A system for ultrasound transmission in materials as defined in claim 7, wherein said signal processing unit comprising a phase comparator, said phase comparator detecting a phase difference between said output electric signal delivered from said point linking two output terminals of said ultrasonic transducers $R_{o1}$ and $R_{o2}$ and said output electric signal delivered from said point linking two output terminals of said ultrasonic transducers $R_{s1}$ and $R_{s2}$, comparing said phase difference with that corresponding to a standard group of fibers or leaf fragments, and evaluating a filling-density of said examination group of fibers or leaf fragments.

10. A system for ultrasound transmission in materials comprising:
- a reference unit consisting of
  - at least an input ultrasonic transducer $T_o$,
  - at least an output ultrasonic transducer $R_o$ corresponding with said ultrasonic transducer $T_o$, and
  - a reference case having a concavity therein;
- an examination unit consisting of
  - at least an input ultrasonic transducer $T_s$,
  - at least an output ultrasonic transducer $R_s$ corresponding with said ultrasonic transducer $T_s$, and
  - an examination case with a concavity therein having an examination group of fibers or leaf fragments on said concavity; and
- a signal processing unit connected with output terminals of said ultrasonic transducers $R_o$ and $R_s$;
- said ultrasonic transducer $T_o$ receiving an electric signal, transducing said electric signal to an ultrasound, and emitting said ultrasound in air,
- said concavity of said reference case reflecting said ultrasound,
- said ultrasonic transducer $R_o$ receiving said ultrasound reflected by said concavity of said reference case and transducing said ultrasound to an output electric signal,
- said ultrasonic transducer $T_s$ receiving an electric signal, transducing said electric signal to an ultrasound, emitting said ultrasound in air, and making said ultrasound go through said examination group of fibers or leaf fragments,
- said concavity of said examination case reflecting said ultrasound transmitted through said examination group of fibers or leaf fragments, and again making said ultrasound go through said examination group of fibers or leaf fragments,
- said ultrasonic transducer $R_s$ receiving said ultrasound transmitted through said examination group of fibers or leaf fragments and transducing said ultrasound to an output electric signal,
- said signal processing unit detecting a difference between said output electric signals delivered from said ultrasonic transducers $R_o$ and $R_s$, comparing said difference with that corresponding to a standard group of fibers or leaf fragments, and evaluating a filling-density of said examination group of fibers or leaf fragments.

11. A system for ultrasound transmission in materials as defined in claim 10 further comprising an amplifier, an output terminal of said ultrasonic transducer $R_o$ being connected with input terminals of said ultrasonic transducers $T_o$ and $T_s$ via said amplifier, said ultrasonic transducers $T_o$, $R_o$ and said amplifier forming an oscillator with an ultrasonic propagation lane, as a delay element, between said ultrasonic transducers $T_o$ and $R_o$.

12. A system for ultrasound transmission in materials as defined in claim 10, wherein said signal processing unit comprising a phase comparator, said phase comparator detecting a phase difference between said output electric signals delivered from said ultrasonic transducers $R_o$ and $R_s$, comparing said phase difference with that corresponding to a standard group of fibers or leaf fragments, and evaluating a filling-density of said examination group of fibers or leaf fragments.

* * * * *